United States Patent
Qiao et al.

(10) Patent No.: US 11,260,374 B2
(45) Date of Patent: Mar. 1, 2022

(54) CU-BASED CATALYST, ITS PREPARATION PROCESS AND USE THEREOF

(71) Applicants: China Petroleum & Chemical Corporation, Beijing (CN); Dalian Research Institute of Petroleum and Petrochemicals, SINOPEC CORP., Liaoning (CN)

(72) Inventors: Kai Qiao, Liaoning (CN); Feng Zhou, Liaoning (CN); Jie Su, Liaoning (CN); Huixia Ma, Liaoning (CN); Qingtong Zhai, Liaoning (CN); Shumei Zhang, Liaoning (CN)

(73) Assignees: China Petroleum & Chemical Corporation, Beijing (CN); Dalian Research Institute of Petroleum and Petrochemicals, SINOPEC CORP., Liaoning Province (CN)

( * ) Notice: Subject to any disclaimer, the term of this patent is extended or adjusted under 35 U.S.C. 154(b) by 0 days.

(21) Appl. No.: 16/190,924

(22) Filed: Nov. 14, 2018

(65) Prior Publication Data

US 2019/0143307 A1 May 16, 2019

(30) Foreign Application Priority Data

Nov. 14, 2017 (CN) .......................... 201711119001.8
Nov. 14, 2017 (CN) .......................... 201711119002.2

(51) Int. Cl.
*B01J 23/72* (2006.01)
*B01J 23/83* (2006.01)
(Continued)

(52) U.S. Cl.
CPC ........... *B01J 23/8892* (2013.01); *B01J 23/78* (2013.01); *B01J 23/80* (2013.01); *B01J 23/83* (2013.01);
(Continued)

(58) Field of Classification Search
CPC ... B01J 23/78; B01J 23/80; B01J 23/83; B01J 23/8892; B01J 23/8868; B01J 31/0202;
(Continued)

(56) References Cited

U.S. PATENT DOCUMENTS 2,400,409 A * 5/1946 Hale .......................... C07C 1/24
585/610
3,360,567 A 12/1967 Johnson, Jr.
(Continued)

FOREIGN PATENT DOCUMENTS

CN    1289638 A    4/2001
CN    1562934 A    1/2005
(Continued)

OTHER PUBLICATIONS

Machine translation of CN1289638, publication date Apr. 4, 2001.*
(Continued)

*Primary Examiner* — Jun Li
(74) *Attorney, Agent, or Firm* — Novick, Kim & Lee, PLLC; Allen Xue

(57) ABSTRACT

The present invention relates to a Cu-based catalyst, a preparation process thereof and its use as the dehydrogenation catalyst in producing a hydroxyketone compound such as acetoin. Said Cu-based catalyst contains copper, at least one auxiliary metal selected from metal of Group IIA, non-noble metal of Group VIII, metal of Group VIB, metal of Group VIIB, metal of Group IIB and lanthanide metal of periodic table of elements, and an alkali metal, and further contains at least one ketone additive selected from a ketone represented by formula (II) and a ketone represented by formula (II'). Said Cu-based catalyst shows a high the acetoin selectivity as the dehydrogenation catalyst for producing acetoin.

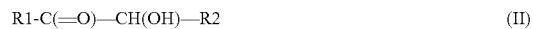

R1-C(=O)—CH(OH)—R2     (II)

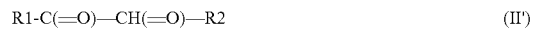

R1-C(=O)—CH(=O)—R2     (II')

In formulae (II) and (II'), each group is defined as in the description.

13 Claims, 1 Drawing Sheet

(51) Int. Cl.

| | | |
|---|---|---|
| *B01J 37/03* | (2006.01) | |
| *B01J 37/08* | (2006.01) | |
| *C07C 45/00* | (2006.01) | |
| *B01J 23/889* | (2006.01) | |
| *B01J 23/78* | (2006.01) | |
| *B01J 37/00* | (2006.01) | |
| *B01J 37/18* | (2006.01) | |
| *B01J 31/02* | (2006.01) | |
| *B01J 23/80* | (2006.01) | |
| *B01J 23/86* | (2006.01) | |
| *B01J 37/34* | (2006.01) | |
| *C07C 49/17* | (2006.01) | |

(52) U.S. Cl.
CPC ......... *B01J 23/868* (2013.01); *B01J 31/0202* (2013.01); *B01J 31/0208* (2013.01); *B01J 37/0009* (2013.01); *B01J 37/031* (2013.01); *B01J 37/036* (2013.01); *B01J 37/08* (2013.01); *B01J 37/18* (2013.01); *B01J 37/343* (2013.01); *C07C 45/002* (2013.01); *B01J 2523/00* (2013.01); *C07C 49/17* (2013.01)

(58) Field of Classification Search
CPC ... B01J 31/0208; B01J 23/868; C07C 45/002; C07C 49/12
See application file for complete search history.

(56) References Cited

U.S. PATENT DOCUMENTS

| | | | | |
|---|---|---|---|---|
| 4,141,919 A * | 2/1979 | Gremmelmaier | ..... | C07C 45/002 568/405 |
| 5,110,954 A * | 5/1992 | Bellis | .......... | C07D 315/00 549/266 |
| 5,654,489 A * | 8/1997 | Kawai | ........... | C07C 45/002 568/361 |
| 2009/0226357 A1* | 9/2009 | Uzio | .................. | C10G 2/331 423/437.2 |
| 2009/0312581 A1* | 12/2009 | Urtel | ................... | B01J 23/8973 568/487 |
| 2018/0290126 A1* | 10/2018 | Kim | .................. | B01J 23/02 |

FOREIGN PATENT DOCUMENTS

| | | | |
|---|---|---|---|
| CN | 102159311 A | 8/2011 | |
| CN | 103044367 A | 4/2013 | |
| CN | 103551154 A | 2/2014 | |
| CN | 105087057 A | 11/2015 | |
| CN | 105363456 A | 3/2016 | |
| EP | 0350762 A1 * | 1/1990 | .......... C07C 45/002 |
| EP | 1586548 A1 | 10/2005 | |
| JP | S5643237 A | 4/1981 | |
| JP | 2005211881 A | 11/2005 | |
| JP | 2008308411 A | 12/2008 | |

OTHER PUBLICATIONS

Conversion of 2,3-Butanediol to Butenes over Bifuncational Catalysts in a Single Reactor, Journal of Catalysis, vol. 330, 2015, p. 222-237.*

Inui et al (Direct synthesis of ethyl acetate from ethanol over Cu—Zn—Zr—Al—O catalyst, Applied Catalysis A: General 237 (2002), 53-61).*

Zheng, Quanxing, "Conversion of 2,3-butanediol over bifunctional catalysts", Dissertation, 2016, pp. 1-241, Department of Chemical Engineering, College of Engineering, Kansas State University, Manhattan, Kansas, Jan. 1, 2016, ISBN: 978-1-369-53378-1.

Tao Feng et al., "Synthesis of supported CuO/palgorskite catalyst and its catalytic performance for 2, 3-butanediol dehydrogenation", Petrochemical Technology, vol. 46, 2017, pp. 979-984.

Xiaozhou Zhang et al., "Progress on Synthesis of Acetoin", Jiangsu Chemical Industry, vol. 29, No. 2, Apr. 2001, pp. 29-31 (English abstract on p. 31).

Sato, Satoshi et al.,Synthesis of a-hydroxyketones from 1,2-diols over Cu-based catalyst, Catalysis Communications 6(9):607-610. DOI:10.1016/j.catcom.2005.05.014.

Torresi, P.A. et al., Upgrading of diols by gas-phase dehydrogenation and dehydration reactions on bifunctional Cu-based oxides, Catal. Sci. Technol., 2014,4, 3203-3213.

* cited by examiner

CU-BASED CATALYST, ITS PREPARATION PROCESS AND USE THEREOF

TECHNICAL FIELD

The present invention relates to a Cu-based catalyst, in particular to a Cu-based dehydrogenation catalyst. The present invention also relates to a preparation process for the Cu-based catalyst and its use as the dehydrogenation catalyst in the production of hydroxyketone compound such as acetoin.

BACKGROUND

Acetoin, also known as 3-hydroxybutanone, is naturally found in many foods such as corn, grapes, apples, meat, etc. It is a widely used flavoring with a pleasant creamy aroma, and mainly used to produce cream, dairy, yogurt, and strawberry-type spices and the like. Acetoin is also an intermediate for many drugs.

The acetaldehyde condensation method is the main production process of food additive grade acetoin in China. Because the thiazole salt catalyst used in this process is expensive and difficult to separate from the product, the commercially available acetoin food additive will contain more or less a certain amount of harmful impurities such as sulfur and nitrogen. For example, CN1562934 discloses an acyloin condensation reaction of acetaldehyde to form acetoin by using acetaldehyde as raw material and a halogenated thiazole salt as catalyst. As a non-acetaldehyde condensation method, Zhang Xiaozhou (Jiangsu Chemical Industry, 2001), 29 (2): 29-31) discloses a method for producing acetoin under the action of hydrogenation catalyst using 2,3-butanedione as raw material.

There is still room for improving the preparation process of acetoin in the prior art in terms of harmful impurity content or industrial implementation or the like.

SUMMARY OF THE INVENTION

The present inventors have found a Cu-based catalyst through a hard and in-depth research on the basis of the prior art, and have further found the at least one of the above technical problems in the prior art can be solved by using the Cu-based catalyst as dehydrogenation catalyst to produce acetoin, and therefore the present invention is accomplished.

Specifically speaking, the present invention relates to the following aspects.

1. A Cu-based catalyst, which contains Cu, at least one auxiliary metal selected from metal of Group IIA (preferably at least one of Mg and Ca), non-noble metal of Group VIII (preferably at least one of Fe and Ni), metal of Group VIB (preferably Cr), metal of Group VIIB (preferably Mn), metal of Group IIB (preferably Zn) and lanthanide metal (preferably ytterbium) of periodic table of elements, an alkali metal and optionally a binder (preferably at least one inorganic binder selected from refractory oxide and aluminosilicate, more preferably at least one inorganic binder selected from alumina, bauxite, pseudo-boehmite, silica, silica-alumina, boehmite, attapulgite, bentonite, kaolin, diatomite and montmorillonite, more preferably at least one inorganic binder selected from alumina, silica, diatomite and kaolin, more preferably alumina), and further contains at least one ketone additive selected from a ketone represented by formula (II) and a ketone represented by formula (II') (preferably acetoin), and optionally a solvent (preferably at least one of C1-6 alcohols, more preferably at least one of C1-6 linear or branched monohydric alcohols, more preferably at least one of methanol and ethanol),

in formulae (II) and (II'), the groups R1 and R2 are identical to or different from each other and each independently represents C1-6 linear or branched alkyl, C1-4 linear or branched alkyl is preferable, methyl or ethyl is more preferable.

2. The Cu-based catalyst according to any of the above aspects, wherein calculated by weight and based on the total weight of said Cu-based catalyst, said catalyst contains 30-60% (preferably 40-50%) of Cu (as CuO), 10-45% (preferably 30-45% or 35-45%) of said at least one auxiliary metal (as oxide), 1-10% (preferably 1-5%) of said alkali metal (as oxide) and 0-30% (preferably 5-15%) of said binder (on a dry basis and as oxide), and relative to 100 parts by weight of said Cu-based catalyst, said ketone additive comprises 0.1 part by weight or more (preferably 0.1-20 parts by weight, 1-10 parts by weight or 1-5 parts by weight), and said solvent comprises 30 parts by weight or less (preferably 10 parts by weight or less, 5 parts by weight or less or 3 parts by weight or less).

3. A process for preparing a Cu-based catalyst, which comprises the steps of: (1) producing a catalyst precursor, wherein said catalyst precursor (calculated by weight and based on the total weight of said catalyst precursor) contains 30-60% (preferably 40-50%) of Cu (as CuO), 10-45% (preferably 30-45% or 35-45%) of at least one auxiliary metal selected from metal of Group IIA (preferably at least one of Mg and Ca), non-noble metal of Group VIII (preferably at least one of Fe and Ni), metal of Group VIB (preferably Cr), metal of Group VIIB (preferably Mn), metal of Group IIB (preferably Zn) and lanthanide metal (preferably ytterbium) of periodic table of elements (as oxide), 1-10% (preferably 1-5%) of an alkali metal (as oxide) and 0-30% (preferably 5-15%) of optionally a binder (preferably at least one inorganic binder selected from refractory oxide and aluminosilicate, more preferably at least one inorganic binder selected from alumina, bauxite, pseudo-boehmite, silica, silica-alumina, boehmite, attapulgite, bentonite, kaolin, diatomite and montmorillonite, more preferably at least one inorganic binder selected from alumina, silica, diatomite and kaolin, more preferably alumina) (on a dry basis and as oxide), and (2-1) contacting a ketone represented by formula (II) (preferably acetoin) with said catalyst precursor to produce said Cu-based catalyst,

R1-C(=O)—CH(OH)—R2 (II)

in formula (II), the groups R1 and R2 are identical to or different from each other and each independently represents C1-6 linear or branched alkyl, preferably C1-4 linear or branched alkyl, more preferably methyl or ethyl, or (1') producing a catalyst precursor, wherein said catalyst precursor (calculated by weight and based on the total weight of said catalyst precursor) contains 30-60% (preferably 40-50%) of Cu (as CuO), 10-45% (preferably 30-45% or 35-45%) of at least one auxiliary metal selected from metal of Group IIA (preferably at least one of Mg and Ca), non-noble metal of Group VIII (preferably at least one of Fe and Ni), metal of Group VIB (preferably Cr), metal of Group VIIB (preferably Mn), metal of Group IIB (preferably Zn) and lanthanide metal (preferably ytterbium) of periodic table of elements (as oxide), optionally an alkali metal and 0-30% (preferably 5-15%) of optionally a binder (preferably at least one inorganic binder selected from refractory oxide and aluminosilicate, more preferably at least one inorganic binder selected from alumina, bauxite, pseudo-boehmite, silica, silica-alumina, boehmite, attapulgite, bentonite, kaolin, diatomite and montmorillonite, more preferably at least one inorganic binder selected from alumina, silica, diatomite and kaolin, more preferably alumina) (on a dry basis and as oxide), and (2-2) contacting a mixture of a ketone represented by formula (II) (preferably acetoin), a solvent (preferably at least one of C1-6 alcohols, more preferably at least one of C1-6 linear or branched monohydric alcohols, more preferably at least one of methanol and ethanol) and optionally an alkali metal precursor with said catalyst precursor (preferably in presence of ultrasonic wave) to produce said Cu-based catalyst, $$R1-C(=O)-CH(OH)-R2 \quad (II)$$

in formula (II), the groups R1 and R2 are identical to or different from each other and each independently represents C1-6 linear or branched alkyl, preferably C1-4 linear or branched alkyl, more preferably methyl or ethyl, (2-3) optionally, after optionally drying, calcining said Cu-based catalyst, wherein, the total of the amount to be used of said alkali metal (as oxide) in step (1') and the amount to be used of said alkali metal precursor (as oxide) in step (2-2) is such an amount that said Cu-based catalyst (calculated by weight and based on the total weight of said Cu-based catalyst) contains 1-10% (preferably 1-5%) of an alkali metal (as oxide), preferably the amount to be used of said alkali metal precursor (as oxide) in step (2-2) is larger than 0, more preferably the amount to be used of said alkali metal precursor (as oxide) in step (2-2) is such an amount that said Cu-based catalyst (calculated by weight and based on the total weight of said Cu-based catalyst) contains 1-10% (preferably 1-5%) of an alkali metal (as oxide).

4. The preparation process according to any of the above or subsequent aspects, wherein in said step (2-1), relative to 100 parts by weight of said catalyst precursor, said ketone represented by formula (II) comprises 0.1 part by weight or more (preferably 0.1-20 parts by weight, 1-10 parts by weight or 1-5 parts by weight), or in said step (2-2), relative to 100 parts by weight of said catalyst precursor, said ketone represented by formula (II) comprises 0.1 part by weight or more (preferably 0.1-20 parts by weight, 1-10 parts by weight or 1-5 parts by weight), and said solvent comprises 30 parts by weight or less (preferably 10 parts by weight or less, 5 parts by weight or less or 3 parts by weight or less).

5. The preparation process according to any of the above or subsequent aspects, wherein in said step (1), a Cu precursor, an auxiliary metal precursor, an alkali metal precursor and optionally a binder precursor are subjected to a co-precipitation to produce said catalyst precursor, or in said step (1'), a Cu precursor, an auxiliary metal precursor, optionally an alkali metal precursor and optionally a binder precursor are subjected to a co-precipitation to produce said catalyst precursor.

6. The preparation process according to any of the above or subsequent aspects, wherein said step (2-1) comprises the following step(s):

(2-1-1) at a temperature of 100-200° C. (preferably 100-150° C.) and under a pressure of 0.1-5 MPa (preferably 0.1-1

MPa), said ketone represented by formula (II) (preferably in a gaseous state or in form of a gas mixture) is contacted with said catalyst precursor for 2-60 hours (preferably 2-48 hours, more preferably 24-48 hours).

7. The preparation process according to any of the above aspects, wherein said step (2-2) comprises the following step(s):

(2-2-1) said catalyst precursor is impregnated with said mixture (preferably in presence of ultrasonic wave) for 5-24 hours (preferably 5-10 hours), (2-2-2) at a temperature of 50-95° C. (preferably 65-70° C.), at least a part (for example, 10% by volume or more, 30% by volume or more, 50% by volume or more, 60% by volume or more, 80% by volume or more, 90% by volume or more, 98% by volume or more, or essentially all) of said solvent is removed by evaporation to produce said Cu-based catalyst, (2-2-3) optionally, at a temperature of 150-350° C. (preferably 300-350° C.) and under a pressure of 0.1-5 MPa (preferably 0.1-1 MPa, more preferably the system self-generated pressure), said Cu-based catalyst is aged for 2-60 hours (preferably 2-48 hours, more preferably 24-48 hours).

8. A process for preparing a hydroxyketone compound (particularly acetoin), which comprises a step of converting a dihydric alcohol represented by formula (I) (preferably 2,3-butanediol) to a hydroxyketone compound represented by formula (II) (preferably acetoin) in presence of a Cu-based catalyst (called as the conversion step), wherein said Cu-based catalyst is at least one of the following Cu-based catalysts, (1) a Cu-based catalyst A, which comprises (calculated by weight and based on the total weight of said Cu-based catalyst):

30-60% (preferably 40-50%) of Cu (as CuO), 10-45% (preferably 30-45% or 35-45%) of at least one auxiliary metal selected from metal of Group IIA (preferably at least one of Mg and Ca), non-noble metal of Group VIII (preferably at least one of Fe and Ni), metal of Group VIB (preferably Cr), metal of Group VIIB (preferably Mn), metal of Group IIB (preferably Zn) and lanthanide metal (preferably ytterbium) of periodic table of elements (as oxide), 1-10% (preferably 1-5%) of an alkali metal (as oxide) and 0-30% (preferably 5-15%) of optionally a binder (preferably at least one inorganic binder selected from refractory oxide and aluminosilicate, more preferably at least one inorganic binder selected from alumina, bauxite, pseudo-boehmite, silica, silica-alumina, boehmite, attapulgite, bentonite, kaolin, diatomite and montmorillonite, more preferably at least one inorganic binder selected from alumina, silica, diatomite and kaolin, more preferably alumina) (on a dry basis and as oxide), (2) Cu-based catalyst B, which is the Cu-based catalyst according to any of the above aspects, (3) a Cu-based catalyst C, which is the Cu-based catalyst prepared with the preparation process according to any of the above aspects, $$R1-CH(OH)-CH(OH)-R2 \quad (I)$$

$$R1-C(=O)-CH(OH)-R2 \quad (II)$$

in formulae (I) and (II), the groups R1 and R2 are identical to or different from each other and each independently represents C1-6 linear or branched alkyl, C1-4 linear or branched alkyl is preferable, methyl or ethyl is more preferable.

9. The preparation process according to any of the above or subsequent aspects, which further comprises a step of contacting said Cu-based catalyst A with said hydroxyketone compound represented by formula (II) (preferably acetoin) for 2-60 hours (preferably 2-48 hours, more preferably 24-48 hours) at a temperature of 150-350° C. (preferably 300-350° C.) and under a pressure of 0.1-5 MPa (preferably 0.1-1 MPa, more preferably the system self-generated pressure) before performing said conversion step, or a step of aging said Cu-based catalyst B or said Cu-based catalyst C for 2-60 hours (preferably 2-48 hours, more preferably 24-48 hours) at a temperature of 150-350° C. (preferably 300-350° C.) and under a pressure of 0.1-5 MPa (preferably 0.1-1 MPa, more preferably the system self-generated pressure), before performing said conversion step.

10. The preparation process according to any of the above or subsequent aspects, which further comprises a step of reducing said Cu-based catalyst in presence of hydrogen at a temperature of 200-400° C. (preferably 200-300° C.) and under a pressure of 0.1-10 MPa (preferably 0.1-1 MPa) before performing said conversion step.

11. The preparation process according to any of the above or subsequent aspects, wherein the reaction conditions of said conversion step comprises: optionally in presence of a diluent (preferably at least one of hydrogen, nitrogen and water vapor, preferably hydrogen), the reaction temperature of 200-300° C., the reaction pressure of 0.01-0.5 MPa, the liquid hourly space velocity of 0.5-10 $h^{-1}$; or in absence of said diluent, the reaction temperature of 250-270° C., the reaction pressure of 0.01-0.2 MPa, the liquid hourly space velocity of 1.5-5 $h^{-1}$; or in presence of said diluent, the reaction temperature of 270-300° C., the reaction pressure of 0.01-0.2 MPa, the liquid hourly space velocity of 5-10 $h^{-1}$, and the molar ratio of said diluent to said dihydric alcohol represented by formula (I) of 0.1-3 (preferably 0.1-1).

12. Use of a Cu-based catalyst as dehydrogenation catalyst (particularly partial dehydrogenation catalyst, more particularly dehydrogenation catalyst or partial dehydrogenation catalyst of 2,3-butanediol), wherein said Cu-based catalyst is at least one of the following Cu-based catalysts, (1) a Cu-based catalyst A, which comprises (calculated by weight and based on the total weight of said Cu-based catalyst):

30-60% (preferably 40-50%) of Cu (as CuO), 10-45% (preferably 30-45% or 35-45%) of at least one auxiliary metal selected from metal of Group IIA (preferably at least one of Mg and Ca), non-noble metal of Group VIII (preferably at least one of Fe and Ni), metal of Group VIB (preferably Cr), metal of Group VIIB (preferably Mn), metal of Group IIB (preferably Zn) and lanthanide metal (preferably ytterbium) of periodic table of elements (as oxide), 1-10% (preferably 1-5%) of an alkali metal (as oxide) and 0-30% (preferably 5-15%) of optionally a binder (preferably at least one inorganic binder selected from refractory oxide and aluminosilicate, more preferably at least one inorganic binder selected from alumina, bauxite, pseudo-boehmite, silica, silica-alumina, boehmite, attapulgite, bentonite, kaolin, diatomite and montmorillonite, more preferably at least one inorganic binder selected from alumina, silica, diatomite and kaolin, more preferably alumina) (on a dry basis and as oxide), (2) Cu-based catalyst B, which is the Cu-based catalyst according to any of the above aspects, (3) a Cu-based catalyst C, which is the Cu-based catalyst prepared with the preparation process according to any of the above aspects,

R1-CH(OH)—CH(OH)—R2 (I)

R1-C(=O)—CH(OH)—R2 (II)

in formulae (I) and (II), the groups R1 and R2 are identical to or different from each other and each independently represents C1-6 linear or branched alkyl, C1-4 linear or branched alkyl is preferable, methyl or ethyl is more preferable.

13. A catalyst for producing acetoin, which contains Cu, an auxiliary metal and an alkali metal, and in the final catalyst, calculated as weight percent, contains 40-50% of copper oxide, 35-45% of the auxiliary metal containing oxide, 1-5% of the alkali metal containing oxide, 5-15% of alumina, said auxiliary metal is at least one element selected from ytterbium, nickel and zinc.

14. The catalyst according to any of the above or subsequent aspects, wherein said auxiliary metal containing oxide is one or more of yttria, nickel oxide, zinc oxide.

15. The catalyst according to any of the above aspects, wherein the alkali metal containing oxide is one or more of lithium oxide, sodium oxide, potassium oxide, and antimony oxide.

16. A process for preparing the catalyst according to any of the above aspects, which comprises the steps of:

(1) an aqueous solution A' containing Cu, Al and an auxiliary metal is formulated, an aqueous solution B' containing a precipitant is formulated, the solution A' and the solution B' are added simultaneously under the continuous stirring condition, the precipitation temperature is controlled to 70-95° C., and the pH value is controlled to 8-9, after the completion of the dropwise addition, the resulting mixture is aged and filtered to produce a precipitate C';

(2) the precipitate C' obtained in step (1) is dried, shaped and calcined to produce a catalyst precursor D';

(3) a methanol solution containing acetoin is formulated, a predetermined amount of a hydroxide containing an alkali metal was added to formulate into a solution E', a predetermined amount of the catalyst precursor D' obtained in step (2) is added and soaked under an ultrasonic condition for 5-10 hours, after the completion of soaking, methanol in the solution E' is evaporated at 65-70° C. to dryness to produce a catalyst precursor F';

(4) the catalyst precursor F' obtained in step (3) is disposed in a closed vessel, and let it stand at a temperature of 300-350° C. for 24-48 hours to produce a catalyst precursor G';

(5) the catalyst precursor G' obtained in step (4) is dried and calcined to produce a final catalyst H'.

17. The preparation process according to any of the above or subsequent aspects, wherein in step (1), said copper salt is one or more of copper nitrate, copper chloride, and copper sulfate, said aluminum salt is one or more of aluminum nitrate, aluminum chloride and aluminum sulfate, and said auxiliary metal salt is one or more of a nitrate, a hydrochloride and a sulfate containing ytterbium, nickel or zinc.

18. The preparation process according to any of the above or subsequent aspects, wherein in step (1), said copper salt is copper nitrate, said aluminum salt is aluminum nitrate, said auxiliary metal salt is a nitrate containing ytterbium, nickel or zinc.

19. The preparation process according to any of the above or subsequent aspects, wherein in step (1) of the process according to the present invention, said precipitant is one or more of a hydroxide containing an alkali metal, a bicarbonate containing an alkali metal and a carbonate containing an alkali metal, said aqueous solution containing the precipitant has a concentration of 0.1-1 M as the molar concentration of the alkali metal ion.

20. The preparation process according to any of the above or subsequent aspects, wherein in step (1), said precipitant is a mixture of a hydroxide containing an alkali metal and a bicarbonate containing an alkali metal, said aqueous solution containing the precipitant has a concentration of 0.5-0.8 M as the molar concentration of the alkali metal ion.

21. The preparation process according to any of the above or subsequent aspects, wherein in step (2), said shaping is carried out through a tabletting method, an extrusion method, a drop ball method or a rolling ball granulation method.

22. The preparation process according to any of the above or subsequent aspects, wherein in step (3), said methanol solution containing acetoin has an acetoin fraction of 1-5% by volume.

23. The preparation process according to any of the above or subsequent aspects, wherein in step (3), said hydroxide containing an alkali metal is one or more of sodium hydroxide, potassium hydroxide, lithium hydroxide, and rubidium hydroxide.

24. The preparation process according to any of the above or subsequent aspects, wherein in step (3), said solution E' is used in such an amount that is 2-10 times the volume of the catalyst precursor D'.

25. The preparation process according to any of the above aspects, wherein in step (4), said closed vessel is a crystallization vessel.

26. A process for producing acetoin, wherein 2,3-butanediol is subjected to a dehydrogenation under the action of a catalyst to produce acetoin, said catalyst (calculated by weight percent) contains:
40-50% of copper oxide,
35-45% of an oxide containing ytterbium, an oxide containing nickel, an oxide containing zinc or a mixture thereof,
1-5% of an alkali metal containing oxide,
5-15% of alumina,
said reaction condition includes: a reaction temperature of 200-300° C.; a reaction pressure of 0.01-0.5 MPa; a liquid hourly space velocity of 0.5-10 $h^{-1}$.

Technical Effect

The Cu-based catalyst according to the present invention, in an embodiment, can be used as a dehydrogenation catalyst to produce acetoin, and shows a high acetoin selectivity.

The process for producing acetoin according to the present invention, in an embodiment, can be utilize a biomass-based material such as 2,3-butanediol as starting material and belongs to a green production technology.

The process for producing acetoin according to the present invention, in an embodiment, has a high selectivity to the acetoin product, and is easy for the large-scale industrial production.

The process for producing acetoin according to the present invention, in an embodiment, has an acetoin product essentially free the harmful impurities such as sulfur and nitrogen.

DETAILED DESCRIPTION OF THE INVENTION

Figure 1:
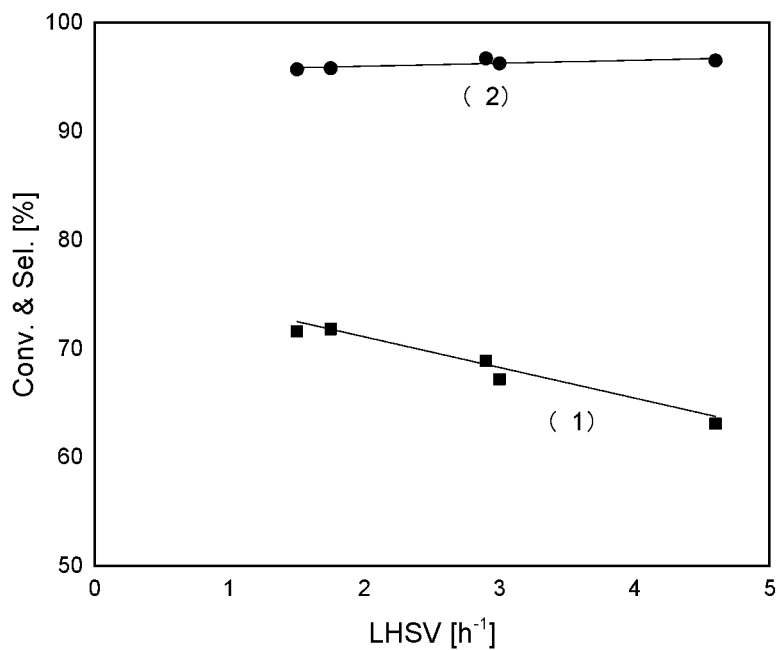
FIG. 1 shows the effect of the space velocity (LHSV) on the 2,3-butanediol conversion (1) and the acetoin selectivity (2) as evaluated in Example 7.

The specific embodiments of the present invention are described in detail below. It should be noted that the scope of the present invention is not limited by the specific embodiments, but is determined by the appended claims.

All publications, patent applications, patents, and other references mentioned in this specification are hereby incorporated by reference in their entirety. Unless defined otherwise, all technical and scientific terms used herein have the meanings commonly understood by those skilled in the art. In case of conflict, the definition in this description shall prevail.

When the present description derives a material, a substance, a method, a step, a device or a component, etc., by the expression "known to those skilled in the art", "prior art" or the like, the object derived from the prefix encompasses those that are routinely used in the art at the time when the present application is filed, but also those that are not currently used, but will become suitable for similar purposes, as recognized in the art.

In the context of the present invention, the so-called "oxide" means either the mentioned metal element is present as a stable metal oxide, or the mentioned metal element acquiescently represents the corresponding oxide of the metal in case of the content analysis for the metal element so that the accurate content of said metal element in the catalyst or the catalyst precursor can be accurately expressed. Those skilled in the art can easily calculate the content of the elementary substance of the metal element in the catalyst or the catalyst precursor according to the content of the oxide in the catalyst or the catalyst precursor, and the metal content as oxide does not mean said metal element in the catalyst or the catalyst precursor is present in form of the oxide structure. For example, the oxide of K refers to K2O, which only means in the catalyst or the catalyst precursor, the content of K is expressed on the calculation basis of K2O, rather than the element K must be present in form of K2O.

In the context of the present invention, the contents of Cu, the auxiliary metal, the alkali metal and the binder can be measured by X-ray fluorescence (XRF), or other methods such as gravimetric method, inductively coupled plasma emission spectroscopy (ICP) and other methods for determining the contents of the involved elements.

In the context of the present invention, the contents of the ketone additive and the solvent are determined based on the weight difference subtraction and the chromatography. The determination method used in the present invention is as follows: a quantitative amount of the catalyst or the catalyst precursor containing the ketone additive and the solvent (the quantitative amount is recorded as m1) is placed in a sample tube such as a sample tube using a chemical adsorption instrument or a thermogravimetric analyzer, or a fixed-bed tubular reactor. An inert gas (helium) is continuously passed from a side of the sample tube to the other side to go into a low temperature (−20° C.) cold trap. The sample tube is heated to 20° C. above the boiling point of the used ketone additive or the used solvent and stayed for more than 2 hours. The liquid W1 in the cold trap is collected and weighed (the mass is recorded as m2), which is the total amount of the ketone additive and the solvent. The mass fractions of the ketone additive and the solvent in W1 is determined by gas chromatography, and accordingly the mass of the ketone additive (denoted as m3) and the mass of the solvent (denoted as m4) in W1 can be calculated. The content of the ketone additive in the catalyst or the catalyst precursor=m3/m1×100; and the content of the solvent in the catalyst or the catalyst precursor=m4/m1×100.

All percentages, parts, ratios, etc. mentioned in this description are by weight and all pressures are gauge pressures, unless expressly stated otherwise.

In the context of the present specification, any two or more aspects or embodiments of the present invention may be arbitrarily combined, and the technical solutions thus formed are part of the original disclosure of the present description, and also fall within the protection scope of the present invention.

According to an embodiment of the present invention, it relates to a Cu-based catalyst, in particular to a dehydrogenation Cu-based catalyst.

According to an embodiment of the present invention, said Cu-based catalyst at least contains Cu, an auxiliary metal and an alkali metal.

According to an embodiment of the present invention, calculated by weight and based on the total weight of said Cu-based catalyst, said Cu-based catalyst contains 30-60%, preferably 40-50% of Cu (as CuO).

According to an embodiment of the present invention, said auxiliary metal can be selected from metal of Group IIA, non-noble metal of Group VIII, metal of Group VIB, metal of Group VIIB, metal of Group IIB or lanthanide metal of periodic table of elements. These auxiliary metals can be used alone, or in combination of two or more in any ratio. As said metal of Group IIA, specifically for example Mg, Ba, Sr or Ca can be exemplified, Mg or Ca is preferable. These metals can be used alone, or in combination of two or more in any ratio. As said non-noble metal of Group VIII, specifically for example Fe, Co or Ni can be exemplified, Fe or Ni is preferable. These metals can be used alone, or in combination of two or more in any ratio. As said metal of Group VIB, specifically for example Cr, Mo or W can be exemplified, Cr is preferable. These metals can be used alone, or in combination of two or more in any ratio. As said metal of Group VIIB, specifically for example Mn or Re can be exemplified, Mn is preferable. These metals can be used alone, or in combination of two or more in any ratio. As said metal of Group IIB, specifically for example Zn or Cd can be exemplified, Zn is preferable. These metals can be used alone, or in combination of two or more in any ratio. As said lanthanide metal, specifically for example La, Ce, Pr, Yb or Lu can be exemplified, Yb is preferable. These metals can be used alone, or in combination of two or more in any ratio.

According to an embodiment of the present invention, calculated by weight and based on the total weight of said Cu-based catalyst, said Cu-based catalyst contains 10-45%, preferably 30-45% or 35-45% of said auxiliary metal (as oxide).

According to an embodiment of the present invention, as said alkali metal, specifically for example Li, Na, K, Rb and Cs can be exemplified, Na and K, particularly K are preferable. These alkali metals can be used alone, or in combination of two or more in any ratio.

According to an embodiment of the present invention, calculated by weight and based on the total weight of said Cu-based catalyst, said Cu-based catalyst contains 1-10%, preferably 1-5% of said alkali metal (as oxide).

According to an embodiment of the present invention, said Cu-based catalyst optionally further contains a binder. As said binder, any binder conventionally used in the production of the dehydrogenation catalyst in the art can be exemplified, specifically for example refractory oxide and aluminosilicate can be exemplified. These binders can be used alone, or in combination of two or more in any ratio. As said refractory oxide, specifically for example alumina, bauxite, pseudo-boehmite, silica and silica-alumina can be exemplified. These refractory oxides can be used alone, or in combination of two or more in any ratio. As said aluminosilicate, for example boehmite, attapulgite, bentonite, kaolin, diatomite and montmorillonite can be exemplified. These aluminosilicates can be used alone, or in combination of two or more in any ratio. As said binder, alumina, silica, diatomite and kaolin are preferable, and alumina is more preferable.

According to an embodiment of the present invention, calculated by weight and based on the total weight of said Cu-based catalyst, said Cu-based catalyst contains 0-30%, preferably 5-15% of said binder (on a dry basis and as oxide).

According to an embodiment of the present invention, said Cu-based catalyst further contains a ketone additive. As said ketone additive, for example a ketone represented by formula (II) or a ketone represented by formula (II'), in particular acetoin can be exemplified. These ketone additives can be used alone, or in combination of two or more in any ratio.

$$R1-C(=O)-CH(OH)-R2 \quad (II)$$

$$R1-C(=O)-CH(=O)-R2 \quad (II')$$

in formulae (II) and (II'), the groups R1 and R2 are identical to or different from each other and each independently represents C1-6 linear or branched alkyl. As said C1-6 linear or branched alkyl, C1-4 linear or branched alkyl is preferable, methyl or ethyl is more preferable.

According to an embodiment of the present invention, relative to 100 parts by weight of said Cu-based catalyst, said ketone additive comprises 0.1 part by weight or more, preferably 0.1-20 parts by weight, 1-10 parts by weight or 1-5 parts by weight.

According to an embodiment of the present invention, said Cu-based catalyst optionally further contains a solvent, in particular an organic solvent. As said organic solvent, for example, any organic solvent that can dissolve said ketone additive, more specifically C1-6 alcohol, in particular C1-6 linear or branched monohydric alcohol, preferably methanol and ethanol can be exemplified. These solvents can be used alone, or in combination of two or more in any ratio.

According to an embodiment of the present invention, relative to 100 parts by weight of said Cu-based catalyst, said solvent comprises 30 parts by weight or less, preferably 10 parts by weight or less, 5 parts by weight or less or 3 parts by weight or less.

According to an embodiment of the present invention, said Cu-based catalyst can be a granular material or a powdery material, and there is no limitation thereto. Because the ketone additive, optionally the solvent and the like are present, said catalyst can be present in a humidification state. In addition, as the shape of said granule, various shapes known in the art and conventionally used as the dehydrogenation catalyst granule can be exemplified, and for example, sphere shape, column shape, sheet shape and the like can be further exemplified. These shapes can be obtained by those skilled in the art through any known conventional method in the art, and there is no limitation thereto.

According to an embodiment of the present invention, said Cu-based catalyst can be prepared according to the preparation process of the present invention, but the preparation process for said Cu-based catalyst is not limited thereto. Here, as said preparation process, it generally comprises step (1) and step (2-1), or comprises step (1') and step (2-2).

Step (1): the preparation of catalyst precursor.

According to an embodiment of the present invention, said catalyst precursor at least contains Cu, an auxiliary metal and an alkali metal.

According to an embodiment of the present invention, calculated by weight and based on the total weight of said catalyst precursor, said catalyst precursor contains 30-60%, preferably 40-50% of Cu (as CuO).

According to an embodiment of the present invention, said auxiliary metal can be selected from metal of Group IIA, non-noble metal of Group VIII, metal of Group VIB, metal of Group VIIB, metal of Group IIB or lanthanide metal of periodic table of elements. These auxiliary metals can be used alone, or in combination of two or more in any ratio. As said metal of Group IIA, specifically for example Mg, Ba, Sr or Ca can be exemplified, Mg or Ca is preferable. These metals can be used alone, or in combination of two or more in any ratio. As said non-noble metal of Group VIII, specifically for example Fe, Co or Ni can be exemplified, Fe or Ni is preferable. These metals can be used alone, or in combination of two or more in any ratio. As said metal of Group VIB, specifically for example Cr, Mo or W can be exemplified, Cr is preferable. These metals can be used alone, or in combination of two or more in any ratio. As said metal of Group VIIB, specifically for example Mn or Re can be exemplified, Mn is preferable. These metals can be used alone, or in combination of two or more in any ratio. As said metal of Group IIB, specifically for example Zn or Cd can be exemplified, Zn is preferable. These metals can be used alone, or in combination of two or more in any ratio. As said lanthanide metal, specifically for example La, Ce, Pr, Yb or Lu can be exemplified, Yb is preferable. These metals can be used alone, or in combination of two or more in any ratio.

According to an embodiment of the present invention, calculated by weight and based on the total weight of said catalyst precursor, said catalyst precursor contains 10-45%, preferably 30-45% or 35-45% of said auxiliary metal (as oxide).

According to an embodiment of the present invention, as said alkali metal, specifically for example Li, Na, K, Rb and Cs, preferably Na and K, in particular K can be exemplified. These alkali metals can be used alone, or in combination of two or more in any ratio.

According to an embodiment of the present invention, calculated by weight and based on the total weight of said catalyst precursor, said catalyst precursor contains 1-10%, preferably 1-5% of said alkali metal (as oxide).

According to an embodiment of the present invention, said catalyst precursor optionally further contains a binder. As said binder, any binder conventionally used in the production of the dehydrogenation catalyst in the art can be exemplified, specifically for example refractory oxide and aluminosilicate can be exemplified. These binders can be used alone, or in combination of two or more in any ratio. As said refractory oxide, specifically for example alumina, bauxite, pseudo-boehmite, silica and silica-alumina can be exemplified. These refractory oxides can be used alone, or in combination of two or more in any ratio. As said aluminosilicate, for example boehmite, attapulgite, bentonite, kaolin, diatomite and montmorillonite can be exemplified. These aluminosilicates can be used alone, or in combination of two or more in any ratio. As said binder, alumina, silica, diatomite and kaolin are preferable, and alumina is more preferable.

According to an embodiment of the present invention, calculated by weight and based on the total weight of said catalyst precursor, said catalyst precursor contains 0-30%, preferably 5-15% of said binder (on a dry basis and as oxide).

According to an embodiment of the present invention, said catalyst precursor can be a granular material or a powdery material, and there is no limitation thereto. In addition, as the shape of said granule, various shapes known in the art and conventionally used as the dehydrogenation catalyst granule can be exemplified, and for example, sphere shape, column shape, sheet shape and the like can be further exemplified. These shapes can be obtained by those skilled in the art through any known conventional method in the art, and there is no limitation thereto.

Step (1'): Preparation of the catalyst precursor. Here, said step (1') and said step (1) are completely identical except that in the catalyst precursor in step (1'), said alkali metal is an optional component, thereby its content can be as low as 0. In addition, in the case that the content is not 0, the corresponding numerical range as prescribed hereinbefore for said step (1) may also directly apply to the content of said alkali metal in the catalyst precursor in step (1') too.

According to an embodiment of the present invention, there is no special limitation to the preparation process of said catalyst precursor, provided that the composition of the catalyst precursor as prescribed in the present invention is met. Nevertheless, as the preparation process of said catalyst precursor, specifically for example a method of subjecting a Cu precursor, an auxiliary metal precursor, optionally (for example depending on step (1) or step (1')) an alkali metal precursor and optionally a binder precursor to co-precipitation to produce said catalyst precursor (hereinafter called as co-precipitation method) can be exemplified.

According to an embodiment of the present invention, said co-precipitation method can comprises more than one or all of the following steps from step (1-1) to step (1-3).

Step (1-1): preparing a solution A of a Cu precursor, an auxiliary metal precursor and optionally a binder precursor, preparing a solution B of a precipitant, mixing said solution A and said solution B to produce a precipitate C.

According to an embodiment of the present invention, there is no special limitation to the solvent used in the preparation of said solution A and said solution B, provided that it can solve the corresponding substance and has no unfavorable influence on said co-precipitation method. As the most convenient solvent, for example water can be exemplified. In addition, there is no special limitation in the present invention to the concentration of each of the precursor(s) in said solution A or the concentration of the precipitant in said solution B, and those skilled in the art can freely select the concentration according to the requirements, but for example, the molar concentration of the precipitant in said solution B (as the alkali metal ion) is generally 0.1-1M or 0.5-0.8M.

According to an embodiment of the present invention, as said binder precursor, for example any material known in the art that can be used as the binder precursor of the dehydrogenation catalyst can be exemplified, and there is no special limitation thereto. Specifically for example, refractory oxide, refractory oxide precursor, aluminosilicate and aluminosilicate precursor can be exemplified. These binder precursors can be used alone, or in combination of two or more in any ratio. As said refractory oxide or its precursor, specifically for example aluminum salt, aluminum hydroxide, alumina, alumina sol, bauxite, pseudo-boehmite, silica, water glass, silica sol, silica gel, silicate ester and silica-alumina can be exemplified. These refractory oxides or their precursors can be used alone, or in combination of two or more in any ratio. As said aluminosilicate or its precursor, for example, sodium aluminosilicate, boehmite, attapulgite, bentonite, kaolin, diatomite and montmorillonite can be exemplified. These aluminosilicates or their precursors can be used alone, or in combination of two or more in any ratio. As said binder precursor, it is preferably selected from aluminum salt, aluminum hydroxide, alumina, silica, silica sol, water glass, diatomite and kaolin, more preferably aluminum salt, aluminum hydroxide and alumina, in particular aluminum nitrate. These binder precursors can be used alone, or in combination of two or more in any ratio.

According to an embodiment of the present invention, there is no special limitation to said Cu precursor and said auxiliary metal precursor, and they can be an oxide of the corresponding element or any substance that can form said oxide after calcining, specifically for example an oxide, a hydroxide, an inorganic acid salt and an organic acid salt of the corresponding element (including the hydrates of these compounds), preferably a water-soluble inorganic acid salt and a water-soluble organic acid salt, more preferably hydrohalide salt such as hydrochloride, alkoxide, nitrate, sulfate and acetate, in particular nitrate can be exemplified. These precursors can be used alone, or in combination of two or more in any ratio.

According to an embodiment of the present invention, there is no special limitation to said precipitant, provided that it can change the pH value of said solution A to produce said precipitate C, specifically for example ammonia water, a hydroxide of an alkali metal, a carbonate of an alkali metal and a bicarbonate of an alkali metal can be exemplified. These precipitants can be used alone, or in combination of two or more in any ratio, more particularly a mixture of a hydroxide and a bicarbonate can be used.

According to an embodiment of the present invention, there is no special limitation to the amount to be used of said precipitant or said solution B, and in general it is such an amount that the pH value of the co-precipitation system reaches 7.5-10, preferably 8-9. According to an embodiment of the present invention, in said step (1-1), said mixing can be done with stirring.

According to an embodiment of the present invention, the temperature of said mixing is 50-95° C., preferably 70-95° C.

According to an embodiment of the present invention, after the completion of mixing said solution A and said solution B, the obtained precipitate C is aged at said mixing temperature for 0.5-12 hours, preferably 2-5 hours. Then, said precipitate C is obtained through a conventional separation manner such as filtering.

Step (1-2): Drying and calcining said precipitate C to produce a pre-catalyst precursor D.

According to an embodiment of the present invention, for step (1'), if the content of said alkali metal is 0, said pre-catalyst precursor D is the catalyst precursor in said step (1').

Step (1-3): Preparing a solution E of an alkali metal precursor to impregnate said precipitate C or said pre-catalyst precursor D with said solution E, and then drying and calcining to produce said catalyst precursor F.

According to an embodiment of the present invention, there is no special limitation to the solvent used in preparing said solution E, provided that it can dissolve said alkali metal precursor and has no unfavorable influence on said impregnation. As the most convenient solvent, for example water can be exemplified. In addition, there is no special limitation in the present invention to the concentration of said alkali metal precursor in said solution E, and those skilled in the art can freely select the concentration according to the requirements. According to an embodiment of the present invention, there is no special limitation to said alkali metal precursor, and it can be an oxide of the alkali metal or any substance that can form the oxide of the alkali metal after calcining, specifically for example an oxide, a hydroxide, an inorganic acid salt and an organic acid salt of the alkali metal (including the hydrates of these compounds), in particular a hydroxide of an alkali metal, a carbonate of an alkali metal and a bicarbonate of an alkali metal can be exemplified. These alkali metal precursors can be used alone, or in combination of two or more in any ratio, more particularly a mixture of potassium hydroxide and potassium bicarbonate can be used.

According to an embodiment of the present invention, in said step (1-2) or step (1-3), there is no special limitation to said drying temperature, but it generally is 80-150° C., preferably 100-120° C. Moreover, there is no special limitation to said drying time, but it generally is 2-48 h, preferably 12-24 h.

According to an embodiment of the present invention, in said step (1-2) or step (1-3), there is no special limitation to said calcining temperature, but it generally is 300-500° C., preferably 350-450° C. Moreover, there is no special limitation to said calcining time, but it generally is 2-24 h, preferably 4-6 h. In addition, said calcining is generally carried out in an oxygen-containing atmosphere. As said oxygen-containing atmosphere, specifically for example air can be exemplified.

According to an embodiment of the present invention, in said step (1-2) or step (1-3), a step of shaping is optionally carried out before calcining. Said shaping step can be done according to any conventional manner known in the art, specifically for example a tabletting method, an extrusion method, a drop ball method or a rolling ball granulation method or the like can be exemplified, and there is no special limitation thereto.

According to an embodiment of the present invention, in said shaping step, a shaping auxiliary can be optionally used. Here, as said shaping auxiliary, for example any shaping auxiliary that can be used in the production of the catalyst particles can be exemplified, and there is no special limitation thereto. Specifically for example water, an auxiliary extruding agent, peptizer, a pH adjuster, a pore-forming agent, a lubricant and the like can be exemplified, more particularly for example water, graphite powder, *sesbania* powder, citric acid, methylcellulose, starch, polyvinyl alcohol and polyethylene glycol can be exemplified. These shaping auxiliaries can be used alone, or in combination of two or more in any ratio. In addition, the amount to be used of these shaping auxiliary can refer to the known information in the art, and there is no special limitation thereto.

According to an embodiment of the present invention, in said co-precipitation method, there is no special limitation to the relative ratio of any two of or the amount to be used of each of said Cu precursor, said auxiliary metal precursor, said optional alkali metal precursor and said optional binder precursor, provided that the content of each component of the finally prepared catalyst precursor satisfies the requirement according to any of the above prescriptions of the present invention.

Step (2-1): Contacting a ketone represented by formula (II) with said catalyst precursor to produce said Cu-based catalyst. Here, as said ketone compound, acetoin is preferable.

$$R_1-C(=O)-CH(OH)-R_2 \qquad (II)$$

in formula (II), the groups R1 and R2 are identical to or different from each other and each independently represents C1-6 linear or branched alkyl. As said C1-6 linear or branched alkyl, in particular C1-4 linear or branched alkyl can be exemplified, and preferably methyl or ethyl can be exemplified.

According to an embodiment of the present invention, there is no special limitation to the manner of contacting said ketone represented by formula (II) with said catalyst precursor, specifically for example the manner of adsorbing said catalyst precursor with said ketone represented by formula (II) to a predetermined content can be exemplified.

According to an embodiment of the present invention, said ketone represented by formula (II) can take part in said contacting or adsorbing in a form of gas or a gaseous mixture. For example, in said gas mixture, said ketone represented by formula (II) has a volumetric fraction of generally 1-10%, preferably 1-5%, relative to the total volume of said gas mixture. In addition, as said inert gas, specifically for example nitrogen, helium and argon, preferably nitrogen can be exemplified. These inert gases can be used alone, or in combination of two or more in any ratio.

According to an embodiment of the present invention, as said predetermined content, relative to 100 parts by weight of said catalyst precursor, the content of said ketone compound is generally 0.1 part by weight or more, preferably 0.1-20 parts by weight, 1-10 parts by weight or 1-5 parts by weight.

According to an embodiment of the present invention, said step (2-1) can comprise step (2-1-1).

Step (2-1-1): contacting said ketone represented by formula (II) with said catalyst precursor for 2-60 hours at a temperature of 100-200° C. under a pressure of 0.1-5 MPa.

According to an embodiment of the present invention, in said step (2-1-1), there is no special limitation to the manner of contacting said ketone represented by formula (II) with said catalyst precursor, specifically for example the manner of contacting said ketone represented by formula (II) in form of gas or a gas mixture with said catalyst precursor can be exemplified, or specifically for example the manner of adsorbing said catalyst precursor with said ketone represented by formula (II) in form of gas or a gas mixture to a predetermined content can be exemplified.

According to an embodiment of the present invention, said contacting or adsorbing of said ketone represented by formula (II) can be carried out in form of gas or a gas mixture. For example, in said gas mixture, said ketone represented by formula (II) has a volumetric fraction of generally 1-10%, preferably 1-5%, relative to the total volume of said gas mixture. In addition, as said inert gas, specifically for example nitrogen, helium and argon, preferably nitrogen can be exemplified. These inert gases can be used alone, or in combination of two or more in any ratio.

According to an embodiment of the present invention, as said predetermined content, relative to 100 parts by weight of said catalyst precursor, the content of said ketone compound is generally 0.1 part by weight or more, preferably 0.1-20 parts by weight, 1-10 parts by weight or 1-5 parts by weight.

According to an embodiment of the present invention, in said step (2-1-1), as said temperature, it is generally 100-200° C., preferably 100-150° C.

According to an embodiment of the present invention, in said step (2-1-1), as said pressure, it is generally 0.1-5 MPa, preferably 0.1-1 MPa.

According to an embodiment of the present invention, in said step (2-1-1), as said contacting time, it is generally 2-60 hours, preferably 2-48 hours, more preferably 24-48 hours.

Step (2-2): contacting a mixture of said ketone represented by formula (II), the solvent and optionally the alkali metal precursor with said catalyst precursor (e.g. impregnating or mixing) to produce said Cu-based catalyst.

According to an embodiment of the present invention, said contacting is carried out in presence of ultrasonic wave.

According to an embodiment of the present invention, as said solvent, in particular the organic solvent, for example any organic solvent that can dissolve said ketone compound and optionally said alkali metal precursor can be exemplified, more particularly for example C1-6 alcohol, in particular C1-6 linear or branched monohydric alcohol, preferably methanol and ethanol can be exemplified. These solvents can be used alone, or in combination of two or more in any ratio.

According to an embodiment of the present invention, there is no special limitation to said alkali metal precursor, it can be an oxide of the alkali metal or any substance that can form the oxide of the alkali metal after calcining, specifically for example an oxide, a hydroxide, an inorganic acid salt and an organic acid salt of the alkali metal (including the hydrates of these compounds), in particular a hydroxide of an alkali metal, a carbonate of an alkali metal and a bicarbonate of an alkali metal can be exemplified. These alkali metal precursors can be used alone, or in combination of two or more in any ratio, more particularly a mixture of potassium hydroxide and potassium bicarbonate can be used.

According to an embodiment of the present invention, there is no special limitation to the manner of contacting said mixture with said catalyst precursor, specifically for example the manner of firstly mixing said ketone represented by formula (II) and optionally said alkali metal precursor with said solvent in a predetermined relative ratio, and then mixing or impregnating said catalyst precursor with the resulting mixture in a predetermined relative ratio (until homogeneously) can be exemplified.

According to an embodiment of the present invention, relative to 100 parts by weight of said catalyst precursor, the amount to be used of said ketone compound is generally 0.1 part by weight or more, preferably 0.1-20 parts by weight, 1-10 parts by weight or 1-5 parts by weight.

According to an embodiment of the present invention, relative to 100 parts by weight of said catalyst precursor, the amount to be used of said solvent is generally 30 parts by weight or less, preferably 10 parts by weight or less, 5 parts by weight or less or 3 parts by weight or less.

According to an embodiment of the present invention, as the amount to be used of said optional alkali metal precursor, specifically for example, the total of the amount to be used of said alkali metal (as oxide) in step (1') and the amount to be used of said alkali metal precursor (as oxide) in step (2-2) being such an amount that the finally prepared Cu-based catalyst (calculated by weight and based on the total weight of said Cu-based catalyst) contains 1-10%, preferably 1-5% of the alkali metal (as oxide) can be exemplified. In other words, it is possible to only use said alkali metal in step (1'), or it is possible to only use said alkali metal precursor in step (2-2), or it is possible to use both said alkali metal in step (1') and said alkali metal precursor in step (2-2), provided that the total of the used amounts of two substances must satisfy the previous prescription according to the present invention, i.e. the Cu-based catalyst finally prepared by the said preparation process (calculated by weight and based on the total weight of said Cu-based catalyst) contains 1-10%, preferably 1-5% of an alkali metal (as oxide).

According to an embodiment of the present invention, in order to further improve the performance of the catalyst based on the present invention, the amount to be used of said alkali metal precursor (as oxide) in step (2-2) is generally greater than 0, preferably the amount to be used of said alkali metal precursor (as oxide) in step (2-2) is such an amount that said Cu-based catalyst (calculated by weight and based on the total weight of said Cu-based catalyst) contains 1-10%, preferably 1-5% of an alkali metal (as oxide). In the latter situation, said alkali metal precursor is not an optional component, and said alkali metal precursor is introduced only in said step (2-2).

According to an embodiment of the present invention, said step (2-2) can comprise the following step (2-2-1) and step (2-2-2).

Step (2-2-1): Impregnating said catalyst precursor with said mixture for 5-24 hours to produce an impregnated mixture (called as impregnation step).

According to an embodiment of the present invention, said impregnation is carried out in presence of ultrasonic wave.

According to an embodiment of the present invention, in said step (2-2-1), there is no special limitation to said impregnation temperature and pressure, and those skilled in the art can make a conventional selection, specifically for example the normal temperature and the normal pressure can be exemplified. In addition, as said impregnation time, it is generally 5-24 hours, preferably 5-10 hours.

According to an embodiment of the present invention, in said impregnation step, from the viewpoint of facilitating the implementation, the volumetric fraction of said ketone represented by formula (II) (especially acetoin) in said mixture is generally 1-5% or 1-3%, but the present invention is not limited thereto. In addition, in said impregnation step, from the viewpoint of facilitating the implementation, the amount to be used of said mixture is generally 2-10 times or 2-5 times by volume of said catalyst precursor, but the present invention is not limited thereto.

Step (2-2-2): removing at least a part of said solvent from said impregnated mixture at a temperature of 50-95° C. to produce said Cu-based catalyst.

According to an embodiment of the present invention, in said step (2-2-2), said temperature is generally 50-95° C., preferably 65-70° C.

According to an embodiment of the present invention, in said step (2-2-2), there is no special limitation to the manner of said removing, provided that at least a part of said solvent can be removed from said impregnated mixture, specifically for example the evaporation method and the like can be exemplified.

According to an embodiment of the present invention, in said step (2-2-2), at least a part of said solvent is removed, for example, 10% by volume or more, 30% by volume or more, 50% by volume or more, 60% by volume or more, 80% by volume or more, 90% by volume or more, 98% by volume or more, or substantially all of said solvent is removed.

According to an embodiment of the present invention, said step (2-2) optionally further comprises step (2-2-3).

Step (2-2-3): Aging said Cu-based catalyst for 2-60 hours at a temperature of 150-350° C. and under a pressure of 0.1-5 MPa.

According to an embodiment of the present invention, in said step (2-2-3), said temperature is generally 150-350° C., preferably 300-350° C.

According to an embodiment of the present invention, in said step (2-2-3), said pressure is generally 0.1-5 MPa, preferably 0.1-1 MPa, more preferably the system self-generated pressure.

According to an embodiment of the present invention, in said step (2-2-3), said aging timing is generally 2-60 hours, preferably 2-48 hours, more preferably 24-48 hours. Here, said aging can be carried out in a closed vessel. As said closed vessel, specifically for example a crystallization vessel can be exemplified, but the present invention is not limited thereto.

According to an embodiment of the present invention, after the completion of said step (2-1) or said step (2-2), step (2-3) is further optionally carried out.

Step (2-3): Calcining said Cu-based catalyst after the optional drying.

According to an embodiment of the present invention, in said step (2-3), there is no special limitation to said drying temperature, but it generally is 80-150° C., preferably 100-120° C. Moreover, there is no special limitation to said drying time, but it generally is 2-48 h, preferably 12-24 h. Said drying step is an optional step.

According to an embodiment of the present invention, in said step (2-3), there is no special limitation to said calcining temperature, but it generally is 300-500° C., preferably 350-450° C. Moreover, there is no special limitation to said calcining time, but it generally is 2-24 h, preferably 4-6 h. In addition, said calcining is generally carried out in an oxygen gas-containing atmosphere. As said oxygen gas-containing atmosphere, specifically for example air can be exemplified.

According to an embodiment of the present invention, said preparation process can comprise the following steps: (1) an aqueous solution A' containing Cu, Al and an auxiliary metal is formulated, an aqueous solution B' containing a precipitant is formulated, the solution A' and the solution B' are added simultaneously under the continuous stirring condition, the precipitation temperature is controlled to 70-95° C., and the pH value is controlled to 8-9, after the completion of the dropwise addition, the resulting mixture is aged and filtered to produce a precipitate C';

(2) the precipitate C' obtained in step (1) is dried, shaped and calcined to produce a catalyst precursor D';

(3) a methanol solution containing acetoin is formulated, a predetermined amount of a hydroxide containing an alkali metal was added to formulate into a solution E', a predetermined amount of the catalyst precursor D' obtained in step (2) is added and soaked under an ultrasonic condition for 5-10 hours, after the completion of soaking, methanol in the solution E' is evaporated at 65-70° C. to dryness to produce a catalyst precursor F';

(4) the catalyst precursor F' obtained in step (3) is disposed in a closed vessel, and let it stand at a temperature of 300-350° C. for 24-48 hours to produce a catalyst precursor G';

(5) the catalyst precursor G' obtained in step (4) is dried and calcined to produce said Cu-based catalyst H'.

According to an embodiment of the present invention, it further relates to use of Cu-based catalyst as dehydrogenation catalyst, in particular as 2,3-butanediol dehydrogenation catalyst. As said dehydrogenation catalyst, it can be a partial dehydrogenation catalyst. Herein, the so-called "partial dehydrogenation" means if a compound to be dehydrogenated (for example, 2,3-butanediol) has multiple hydrogen atoms having the same properties in its chemical structural formula, only a part of hydrogen atoms (e.g. one) is removed.

According to an embodiment of the present invention, it further relates to a method of producing a hydroxyketone compound, in particular acetoin. It is specifically stated here, except for the following specified items and contents, any manner and any method conventionally used for the catalytic dehydrogenation reaction in the art can be directly applied to the method of producing said hydroxyketone compound of the present invention, and will not be discussed in details herein.

According to an embodiment of the present invention, the method of producing said hydroxyketone compound comprises a step of converting a dihydric alcohol represented by formula (I) into a hydroxyketone compound represented by formula (II) in presence of a Cu-based catalyst (called as the conversion step).

According to an embodiment of the present invention, in said use or in the production method of said hydroxyketone compound, as said Cu-based catalyst, for example, Cu-based catalyst A, Cu-based catalyst B and Cu-based catalyst C can be exemplified. These Cu-based catalysts can be used alone, or in combination of two or more in any ratio.

According to an embodiment of the present invention, as said Cu-based catalyst B and said Cu-based catalyst C, for example, any of Cu-based catalysts as mentioned previously in the present description can be exemplified. These Cu-based catalysts can be used alone, or in combination of two or more in any ratio.

According to an embodiment of the present invention, said Cu-based catalyst A at least contains Cu, an auxiliary metal and an alkali metal.

According to an embodiment of the present invention, calculated by weight and based on the total weight of said Cu-based catalyst A, said Cu-based catalyst A contains 30-60%, preferably 40-50% of Cu (as CuO).

According to an embodiment of the present invention, said auxiliary metal can be selected from metal of Group IIA, non-noble metal of Group VIII, metal of Group VIB, metal of Group VIIB, metal of Group IIB or lanthanide metal of periodic table of elements. These auxiliary metals can be used alone, or in combination of two or more in any ratio. As said metal of Group IIA, specifically for example Mg, Ba, Sr or Ca can be exemplified, Mg or Ca is preferable. These metals can be used alone, or in combination of two or more in any ratio. As said non-noble metal of Group VIII, specifically for example Fe, Co or Ni can be exemplified, Fe or Ni is preferable. These metals can be used alone, or in combination of two or more in any ratio. As said metal of Group VIB, specifically for example Cr, Mo or W can be exemplified, Cr is preferable. These metals can be used alone, or in combination of two or more in any ratio. As said metal of Group VIIB, specifically for example Mn or Re can be exemplified, Mn is preferable. These metals can be used alone, or in combination of two or more in any ratio. As said metal of Group IIB, specifically for example Zn or Cd can be exemplified, Zn is preferable. These metals can be used alone, or in combination of two or more in any ratio. As said lanthanide metal, specifically for example La, Ce, Pr, Yb or Lu can be exemplified, Yb is preferable. These metals can be used alone, or in combination of two or more in any ratio.

According to an embodiment of the present invention, calculated by weight and based on the total weight of said Cu-based catalyst A, said Cu-based catalyst A contains 10-45%, preferably 30-45% or 35-45% of said auxiliary metal (as oxide).

According to an embodiment of the present invention, as said alkali metal, specifically for example Li, Na, K, Rb and Cs, preferably Na and K, in particular K can be exemplified. These alkali metals can be used alone, or in combination of two or more in any ratio.

According to an embodiment of the present invention, calculated by weight and based on the total weight of said Cu-based catalyst A, said Cu-based catalyst A contains 1-10%, preferably 1-5% of said alkali metal (as oxide).

According to an embodiment of the present invention, said Cu-based catalyst A optionally further contains a binder. As said binder, any binder conventionally used in the production of the dehydrogenation catalyst in the art can be exemplified, specifically for example refractory oxide and aluminosilicate can be exemplified. These binders can be used alone, or in combination of two or more in any ratio. As said refractory oxide, specifically for example alumina, bauxite, pseudo-boehmite, silica and silica-alumina can be exemplified. These refractory oxides can be used alone, or in combination of two or more in any ratio. As said aluminosilicate, for example boehmite, attapulgite, bentonite, kaolin, diatomite and montmorillonite can be exemplified. These aluminosilicates can be used alone, or in combination of two or more in any ratio. As said binder, alumina, silica, diatomite and kaolin are preferable, and alumina is more preferable.

According to an embodiment of the present invention, calculated by weight and based on the total weight of said Cu-based catalyst A, said Cu-based catalyst A contains 0-30%, preferably 5-15% of said binder (on a dry basis and as oxide).

According to an embodiment of the present invention, said Cu-based catalyst A is a catalyst for producing acetoin, which contains Cu, an auxiliary metal and an alkali metal, and in the final catalyst, calculated as weight percent, which contains 40-50% of copper oxide, 35-45% of the auxiliary metal containing oxide, 1-5% of the alkali metal containing oxide, and 5-15% of alumina, said auxiliary metal is at least one element selected from ytterbium, nickel and zinc.

According to an embodiment of the present invention, said Cu-based catalyst A can be a granular material or a powdery material, and there is no limitation thereto. In addition, as the shape of said granule, various shapes known in the art and conventionally used as the dehydrogenation catalyst granule can be exemplified, and for example, sphere shape, column shape, sheet shape and the like can be further exemplified. These shapes can be obtained by those skilled in the art through any known conventional method in the art, and there is no limitation thereto.

According to an embodiment of the present invention, said Cu-based catalyst A can be prepared according to any conventional manner known in the art, or can be also prepared with reference to the method of producing said catalyst precursor as previously described in the present description, and there is no special limitation thereto. According to an embodiment of the present invention, as said dihydric alcohol represented by formula (I), in particular 2,3-butanediol can be exemplified. Herein, as said 2,3-butanediol, for example 2,3-butanediol obtained through olefin hydration or biological fermentation, in particular 2,3-butanediol obtained through biological fermentation can be exemplified.

$$R1-CH(OH)-CH(OH)-R2 \qquad (I)$$

in said formula (I), the groups R1 and R2 are identical to or different from each other and each independently represents C1-6 linear or branched alkyl. Herein as said C1-6 linear or branched alkyl, in particular C1-4 linear or branched alkyl can be exemplified, and preferably methyl or ethyl can be exemplified.

According to an embodiment of the present invention, as said hydroxyketone compound represented by formula (II), in particular acetoin can be exemplified.

R1-C(=O)—CH(OH)—R2 (II)

in formula (II), the groups R1 and R2 are identical to or different from each other and each independently represents C1-6 linear or branched alkyl. Herein as said C1-6 linear or branched alkyl, in particular C1-4 linear or branched alkyl can be exemplified, and preferably methyl or ethyl can be exemplified.

According to an embodiment of the present invention, in order to further improve the technical effect of the present invention on a basis of the present invention, the production method of said hydroxyketone compound optionally further comprises a step of contacting said Cu-based catalyst A with said hydroxyketone compound represented by formula (II) for 2-60 hours at a temperature of 150-350° C. and under a pressure of 0.1-5 MPa before performing said conversion step (called as pre-contacting step).

According to an embodiment of the present invention, in said pre-contacting step, said temperature is generally 150-350° C., preferably 300-350° C.

According to an embodiment of the present invention, in said pre-contacting step, said pressure is generally 0.1-5 MPa, preferably 0.1-1 MPa, more preferably the system self-generated pressure.

According to an embodiment of the present invention, in said pre-contacting step, said contacting time is generally 2-60 hours, preferably 2-48 hours, more preferably 24-48 hours.

According to an embodiment of the present invention, in order to further improve the technical effect of the present invention on a basis of the present invention, the production method of said hydroxyketone compound optionally further comprises a step of aging said Cu-based catalyst B or said Cu-based catalyst C for 2-60 hours at a temperature of 150-350° C. and under a pressure of 0.1-5 MPa before performing said conversion step (called as aging step). An aged Cu-based catalyst is obtained through said aging step.

According to an embodiment of the present invention, in said aging step, said temperature is generally 150-350° C., preferably 300-350° C.

According to an embodiment of the present invention, in said aging step, said pressure is generally 0.1-5 MPa, preferably 0.1-1 MPa, more preferably the system self-generated pressure.

According to an embodiment of the present invention, in said aging step, said aging timing is generally 2-60 hours, preferably 2-48 hours, more preferably 24-48 hours. Herein said aging can be carried out in a closed vessel. As said closed vessel, specifically for example a crystallization vessel can be exemplified, but the present invention is not limited thereto.

According to an embodiment of the present invention, the production method of said hydroxyketone compound optionally further comprises a step of reducing said Cu-based catalyst in presence of hydrogen gas at a temperature of 200-400° C. under a pressure of 0.1-10 MPa before performing said conversion step (called as the reducing step).

According to an embodiment of the present invention, in said the reducing step, said temperature is generally 200-400° C., preferably 200-300° C.

According to an embodiment of the present invention, in said the reducing step, said pressure is generally 0.1-10 MPa, preferably 0.1-1 MPa.

According to an embodiment of the present invention, in said the reducing step, there is no special limitation to the manner of said reducing, and it can be selected based on the common knowledge by those skilled in the art, as along as the expected object for reducing can be accomplished, specifically for example the manner in which a mixed gas of nitrogen and hydrogen having a hydrogen gas volumetric fraction of 10-100% is passed through a catalyst bed layer containing said Cu-based catalyst at said temperature at a linear velocity of not lower than 100 ml/min can be exemplified. The present invention is not limited thereto.

According to an embodiment of the present invention, in said the reducing step, there is no special limitation to said reducing time, and it can be selected based on the common knowledge by those skilled in the art, as along as the expected object for reducing can be accomplished. It is generally not lower than 5 hours.

According to an embodiment of the present invention, in the production method of said hydroxyketone compound, said conversion step can be carried out optionally in presence of a diluent. Herein, as said diluent, for example various diluents that are conventionally used in the dehydrogenation reaction in the art can be exemplified, more specifically for example hydrogen gas, nitrogen and water vapor, preferably hydrogen gas can be exemplified. These diluents can be used alone, or in combination of two or more in any ratio.

According to an embodiment of the present invention, when said diluent is present, the molar ratio of said diluent to said dihydric alcohol represented by formula (I) is generally 0.1-3, preferably 0.1-1.

According to an embodiment of the present invention, in the production method of said hydroxyketone compound, the reaction temperature of said conversion step is generally 200-300° C. In particular, when said diluent is present, the reaction temperature is generally 270-300° C. Alternatively, when said diluent is absent, the reaction temperature is generally 250-270° C.

According to an embodiment of the present invention, in the production method of said hydroxyketone compound, the reaction pressure of said conversion step is generally 0.01-0.5 MPa. In particular, when said diluent is present, the reaction pressure is generally 0.1-0.5 MPa. Alternatively when said diluent is absent, in general, the reaction pressure is preferably 0.01-0.2 MPa.

According to an embodiment of the present invention, in the production method of said hydroxyketone compound, the LHSV of said conversion step is generally 0.5-10 $h^{-1}$. In particular, when said diluent is present, the LHSV is generally 5-10 $h^{-1}$. Alternatively when said diluent is absent, the LHSV is generally 1.5-5 $h^{-1}$.

According to an embodiment of the present invention, the production method of said hydroxyketone compound can be carried out in any reactor that is conventionally used in the art for the catalytic dehydrogenation reaction, specifically for example a fixed bed reactor, a fluidized bed reactor and a moving bed reactor, preferably a fixed bed reactor can be exemplified.

According to an embodiment of the present invention, the present invention relates to a method for producing acetoin, wherein 2,3-butanediol is subjected to a dehydrogenation under the action of a catalyst to produce acetoin, said catalyst (calculated by weight percent) contains 40-50% of copper oxide, 35-45% of an oxide containing ytterbium, an oxide containing nickel, an oxide containing zinc or a mixture thereof, 1-5% of an alkali metal containing oxide, 5-15% of alumina, said reaction condition includes: a reaction temperature of 200-300° C.; a reaction pressure of 0.01-0.5 MPa; a liquid hourly space velocity of 0.5-10 h$^{-1}$.

EXAMPLE

The invention is further illustrated by the following examples, but the invention is not limited to the examples.

In the following examples and comparative examples, all reagents and materials are commercially available.

In the following examples and comparative examples, without the special clarification, the liquid hourly space velocity is based on volume, and each pressure (including reaction pressure) is a gauge pressure.

In the context of the present specification, including the examples and the comparative examples, as follows the 2,3-butanediol conversion ($x_{2,3\text{-}butanediol}$) is calculated according to the following equation $$x_{2,3\text{-}butanediol} = \frac{f_{2,3\text{-}butanediol} - p_{2,3\text{-}butanediol}}{f_{2,3\text{-}butanediol}} \times 100\%$$

the acetoin selectivity ($s_{acetoin}$) is calculated according to the following equation $$s_{acetoin} = \frac{p_{acetoin} - f_{acetoin}}{f_{2,3\text{-}butanediol} - p_{2,3\text{-}butanediol}} \times 100\%$$

the acetoin yield ($y_{acetoin}$) is calculated according to the following equation $$y_{acetoin} = \frac{p_{acetoin} - f_{acetoin}}{f_{2,3\text{-}butanediol}} \times 100\%$$

wherein $f_{2,3\text{-}butanediol}$ and $f_{acetoin}$ respectively represent the molar amounts of 2,3-butanediol and acetoin in the raw material, $p_{2,3}$-butanediol and $p_{acetoin}$ respectively represent the molar amounts of 2,3-butanediol and acetoin in the product.

Example 1

The preparation of the Cu-based catalyst H1 was as follows:

(1-1) 122 g of copper nitrate, 103 g of ytterbium nitrate and 88 g of aluminum nitrate were dissolved in 1 L of deionized water to formulate a solution A1. 16 g of potassium hydroxide and 24 g of potassium bicarbonate were dissolved in 1 L of deionized water to formulate a solution B1. 1 L of deionized water was added to a 5 L beaker, and warmed up and maintained at 75° C., and under a continuous stirring, to the beaker were added dropwisely the solutions A1 and B1, and the pH value was maintained at about 8.0. After the completion of the dropwise addition, the mixture was continuously stirred for 2 hours, then aged by standing for 2 hours, and filtered to produce a precipitate C1.

(1-2) The precipitate C1 was placed at 110° C. and dried for 24 hours, and then calcined at 400° C. for 5 hours. Then a graphite powder as lubricant was added in an amount of 3% by weight of the precipitate. The mixture was shaped by tabletting, and calcined at 400° C. for 5 hours to produce a cylindrical catalyst precursor D1 having a diameter of 4.5-5.5 mm and a height of 5-5.5 mm.

(1-3) 0.35 g of KOH was added to 15 ml of deionized water to prepare a solution E1. 10 g of the catalyst precursor D1 (about 7.5 ml) was added to the solution E1, and soaked under an ultrasonic condition for 8 hours. After the completion of soaking, removing water by evaporating the solution E1 at 85° C. to dryness, drying at 110° C. for 24 hours, then calcining at 400° C. for 5 hours were carried out to produce a catalyst H1.

By elemental analysis, the catalyst H1 had the CuO content by weight of 40.6%, the Yb2O3 content by weight of 44.5%, the K2O content by weight of 2.7%, and the Al2O3 content by weight of 12.2%.

The catalyst H1 was reduced with a mixed gas of nitrogen and hydrogen having a hydrogen gas volumetric fraction of 10% at normal pressure at 260° C. for 5 hours before it was used in the dehydrogenation reaction of dihydric alcohol to prepare the hydroxyketone. After the completion of the reduction, the feeding was switched to the starting reaction material to carry out the reaction.

Example 2

The preparation of the Cu-based catalyst H2 was as follows:

(1) The catalyst H1 prepared in Example 1 was used as the catalyst precursor;

(2) The above catalyst precursor H1 was ground into powder. The powder H1 was added to the straight sample tube of TP-5082-type chemisorption instrument, and warmed up to 100° C. in the nitrogen atmosphere and kept constantly at this temperature. The feeding was switched to a mixed gas of acetoin/nitrogen having an acetoin volumetric fraction of 1% and treated for 48 hours. The reaction system was cooled and removed to produce a catalyst H2.

By elemental analysis, the catalyst H2 had the CuO content by weight of 40.1%, the Yb2O3 content by weight of 44.0%, the K2O content by weight of 2.6%, the Al2O3 content by weight of 12.1%, and the acetoin content by weight of 1.2%.

The catalyst H2 was subjected to the following pre-treatment before it was used in the dehydrogenation reaction of dihydric alcohol to prepare the hydroxyketone:

(3-1) 10 g of the catalyst H2 was loaded in a 20 ml stainless crystallization vessel, and nitrogen was introduced until the pressure reached 1 MPa. The crystallization vessel was placed in an oven at 300° C., and the treatment was carried out for 48 hours;

(3-2) the catalyst H2 obtained after the treatment in step (3-1) was reduced with a mixed gas of nitrogen and hydrogen having a hydrogen gas volumetric fraction of 10% at normal pressure at 260° C. for 5 hours. After the completion of the reduction, the feeding was switched to the starting reaction material to carry out the reaction.

Examples 3-7

The pre-reduced catalyst H1 obtained in Example 1 and the pre-treated catalyst H2 obtained in Example 2 were used as catalyst respectively to investigate the reaction performance for the production of acetoin by the direct dehydrogenation of 2,3-butanediol in a fixed bed reactor having an inner diameter of 10 mm. The experiment results were listed in Table 1.

TABLE 1

| Example | Catalyst | Reaction temperature (° C.) | Reaction pressure (MPa) | LHSV (h$^{-1}$) | Diluent | 2,3-butanediol conversion (%) | Acetoin selectivity (%) | Acetoin yield (%) |
| --- | --- | --- | --- | --- | --- | --- | --- | --- |
| 3 | H1 | 230 | 0.1 | 3 | No | 55.6 | 69.4 | 38.6 |
| 4 | H2 | 230 | 0.1 | 3 | No | 49.5 | 97.1 | 48.1 |
| 5 | H2 | 250 | 0.2 | 3 | No | 67.2 | 96.2 | 64.7 |
| 6 | H2 | 270 | 0.2 | 3 | No | 78.8 | 93.9 | 74.0 |
| 7 | H2 | 300 | 0.01 | 3 | No | 79.2 | 93.1 | 73.7 |

Example 8

The preparation of the Cu-based catalyst H3 was as follows:

(1) The preparation of the catalyst precursor was carried out in the following steps:

(1-1) 137 g of copper nitrate, 136 g nickel nitrate and 111 g of aluminum nitrate were dissolved in 1 L of deionized water to formulate a solution A3. 30 g of potassium hydroxide and 24 g of potassium bicarbonate were dissolved in 1 L of deionized water to formulate a solution B3. 1 L of deionized water was added to a 5 L beaker, and warmed up and maintained at 75° C., and under a continuous stirring, to the beaker were added dropwisely the solutions A3 and B3, and the pH value was maintained at about 9.0. After the completion of the dropwise addition, the mixture was continuously stirred for 2 hours, then aged by standing for 2 hours, and filtered to produce a precipitate C3.

(1-2) The precipitate C3 was placed at 110° C. and dried for 24 hours, and then calcined at 400° C. for 5 hours. Then a graphite powder as lubricant was added in an amount of 3% by weight of the precipitate. The mixture was shaped by tabletting, and calcined at 400° C. for 5 hours to produce a cylindrical catalyst precursor D3 having a diameter of 4.5-5.5 mm and a height of 5-5.5 mm.

(1-3) 0.65 g of KOH was added to 15 ml of deionized water to prepare a solution E3. 10 g of the catalyst precursor D3 (about 7.5 ml) was added to the solution E3, and soaked under an ultrasonic condition for 10 hours. After the completion of soaking, removing water by evaporating the solution E3 at 85° C. to dryness, drying at 110° C. for 24 hours, then calcining at 400° C. for 5 hours were carried out to produce a catalyst F3.

(2) The preparation of the Cu-based catalyst H3 was carried out in the following steps:

(2-1) The above catalyst precursor F3 was added to a fixed bed reactor having an inner diameter of 10 mm, and warmed up to 150° C. in the nitrogen atmosphere and kept constantly at this temperature. The feeding was switched to a mixed gas of acetoin/nitrogen having an acetoin volumetric fraction of 5% and treated for 24 hours. The reaction system was cooled and removed to produce a final catalyst H3.

By elemental analysis, the catalyst H3 had the CuO content by weight of 43.8%, the NiO content by weight of 35.0%, the K2O content by weight of 4.6%, the Al2O3 content by weight of 14.4%, the acetoin content by weight of 2.2%.

The catalyst H3 was subjected to the following pre-treatment before it was used in the dehydrogenation reaction of dihydric alcohol to prepare the hydroxyketone:

(3-1) 10 g of the catalyst H3 was loaded in a 20 ml stainless crystallization vessel, and nitrogen was introduced until the pressure reached 0.1 MPa. The crystallization vessel was placed in an oven at 350° C., and the treatment was carried out for 24 hours;

(3-2) the catalyst H3 obtained after the treatment in step (3-1) was reduced with a mixed gas of nitrogen and hydrogen having a hydrogen gas volumetric fraction of 10% at normal pressure at 230° C. for 8 hours. After the completion of the reduction, the feeding was switched to the starting reaction material to carry out the reaction.

Example 9

The pre-treated catalyst H3 obtained in Example 8 was used as catalyst to investigate the effect of LHSV on the reaction performance for the production of acetoin by the direct dehydrogenation of 2,3-butanediol in a fixed bed reactor having an inner diameter of 10 mm. The reaction temperature was 250° C., and the reaction pressure was 0.2 MPa. The experiment results were listed in FIG. 1.

Example 10

The preparation of the Cu-based catalyst H'4 was as follows:

(1) The preparation of the catalyst precursor F'4 was carried out in the following steps:

(1'-1) 137 g of copper nitrate, 103 g of ytterbium nitrate and 45 g of aluminum nitrate were dissolved in 1 L of deionized water to formulate a solution A'4. 30 g of potassium hydroxide and 12 g of potassium bicarbonate were dissolved in 1 L of deionized water to formulate a solution B'4. 1 L of deionized water was added to a 5 L beaker, and warmed up and maintained at 70° C., and under a continuous stirring, to the beaker were added dropwisely the solutions A'4 and B'4, and the pH value was maintained at about 9.0. After the completion of the dropwise addition, the mixture was continuously stirred for 2 hours, then aged by standing for 2 hours, and filtered to produce a precipitate C'4.

(1'-2) The precipitate C'4 was placed at 110° C. and dried for 24 hours, and then calcined at 400° C. for 5 hours. Then a graphite powder as lubricant was added in an amount of 3% by weight of the precipitate. The mixture was shaped by tabletting, and calcined at 400° C. for 5 hours to produce a cylindrical catalyst precursor D'4 having a diameter of 2.5-3.5 mm and a height of 2.5-3.5 mm.

(1'-3) 0.50 g of KOH was added to 15 ml of deionized water to prepare a solution E'4. 10 g of the catalyst precursor D'4 (about 7.5 ml) was added to the solution E'4, and soaked under an ultrasonic condition for 10 hours. After the completion of soaking, removing water by evaporating the solution E'4 at 85° C. to dryness, drying at 110° C. for 24 hours, then calcining at 400° C. for 5 hours were carried out to produce a catalyst F'4.

(2) The preparation of the Cu-based catalyst H'4 was as follows:

(2-2-1) 0.61 g of acetoin was dissolved in 30 ml of methanol to formulate a solution G'4. The catalyst precursor F'4 was ground into powder. 10 g of the catalyst precursor F'4 powder was added to the solution G'4, and soaked for 6 hours by continuously stirring at room temperature (20-30° C.);

(2-2-2) After the completion of the soaking in step (2-2-1), 98% by volume of the liquid in the solution E'4 was removed by evaporating at 70° C. to produce a final Cu-based catalyst F'4.

By elemental analysis, the catalyst H'4 had the CuO content by weight of 43.9%, the Yb2O3 content by weight of 41.4%, the K2O content by weight of 3.2%, the Al2O3 content by weight of 6.7%, the acetoin content by weight of 3.9%, and the methanol content by weight of 1.0%.

The catalyst H'4 was subjected to the following pre-treatment before it was used in the dehydrogenation reaction of dihydric alcohol to prepare the hydroxyketone:

(3-1) 10 g of the catalyst H'4 was loaded in a 20 ml stainless crystallization vessel. The crystallization vessel was kept under a self-generated pressure, and placed in an oven at 300° C. to let it stand for 36 hours;

(3-2) The catalyst H'4 obtained after the treatment in step (3-1) was reduced with a mixed gas of nitrogen and hydrogen having a hydrogen gas volumetric fraction of 10% at normal pressure at 250° C. for 7 hours. After the completion of the reduction, the feeding was switched to the starting reaction material to carry out the reaction.

Examples 11-14

The pre-treated catalyst H'4 obtained in Example 10 was used as catalyst to investigate the effect of diluent on the reaction performance for the production of acetoin by the dehydrogenation of 2,3-butanediol in a fixed bed reactor having an inner diameter of 10 mm. The experiment results were listed in Table 2.

formulate a solution B'5. 1 L of deionized water was added to a 5 L beaker, and warmed up and maintained at 80° C., and under a continuous stirring, to the beaker were added dropwisely the solutions A'5 and B'5, and the pH value was maintained at about 8.0. After the completion of the dropwise addition, the mixture was continuously stirred for 2 hours, then aged by standing for 2 hours, and filtered to produce a precipitate C'5.

(1'-2) The precipitate C'5 was placed at 110° C. and dried for 24 hours, and then calcined at 400° C. for 5 hours. Then a graphite powder as lubricant was added in an amount of 3% by weight of the precipitate. The mixture was shaped by tabletting, and calcined at 400° C. for 5 hours to produce a cylindrical catalyst precursor D'5 having a diameter of 2.5-3.5 mm and a height of 2.5-3.5 mm.

(1'-3) 0.10 g of KOH was added to 15 ml of deionized water to prepare a solution E'5. 10 g of the catalyst precursor D'5 (about 7.5 ml) was added to the solution E'5, and soaked under an ultrasonic condition for 10 hours. After the completion of soaking, removing water by evaporating the solution E'5 at 85° C. to dryness, drying at 110° C. for 24 hours, then calcining at 400° C. for 5 hours were carried out to produce a catalyst precursor F'5.

(2) The preparation of the Cu-based catalyst H'5 was as follows:

(2-2-1) 0.77 g of acetoin was dissolved in 37.5 ml of methanol to formulate a solution G'5. 10 g of the catalyst precursor F'5 was added to the solution G'5, and soaked for 6 hours by stirring under an ultrasonic condition at room temperature (20-30° C.);

(2-2-2) After the completion of the soaking in step (2-2-1), 97% by volume of the liquid in the solution E'5 was removed by evaporating at 65° C. to produce a final Cu-based catalyst F'5.

By elemental analysis, the catalyst H'5 had the CuO content by weight of 45.6%, the NiO content by weight of 36.9%, the K2O content by weight of 1.0%, the Al2O3 content by weight of 9.4%, the acetoin content by weight of 4.4%, the methanol content by weight of 2.8%.

The catalyst H'5 was subjected to the following pre-treatment before it was used in the dehydrogenation reaction of dihydric alcohol to prepare the hydroxyketone:

(3-1) 10 g of the catalyst H'5 was loaded in a 20 ml stainless crystallization vessel. The crystallization vessel

TABLE 2

| Example | Reaction temperature (° C.) | Reaction pressure (MPa) | LHSV ($h^{-1}$) | Diluent | Diluent/2,3-butanediol molar ratio | 2,3-butanediol conversion (%) | Acetoin selectivity (%) | Acetoin yield (%) |
|---|---|---|---|---|---|---|---|---|
| 11 | 250 | 0.2 | 5 | nitrogen | 1 | 71.5 | 91.0 | 65.1 |
| 12 | 270 | 0.2 | 7 | water vapor | 1 | 69.7 | 87.5 | 61.0 |
| 13 | 250 | 0.1 | 5.5 | hydrogen gas | 1 | 64.3 | 97.3 | 62.6 |
| 14 | 260 | 0.1 | 7 | No | 0 | 63.1 | 93.5 | 59.0 |

Example 15

The preparation of the Cu-based catalyst H'5 was as follows:

(1') The preparation of the catalyst precursor F'5 was carried out in the following steps:

(1'-1) 152 g of copper nitrate, 156 g nickel nitrate and 67 g of aluminum nitrate were dissolved in 1 L of deionized water to formulate a solution A'5. 33.6 g of potassium hydroxide was dissolved in 1 L of deionized water to was kept under a self-generated pressure, and placed in an oven at 350° C. to let it stand for 24 hours;

(3-2) The catalyst H'5 obtained after the treatment in step (3-1) was reduced with a mixed gas of nitrogen and hydrogen having a hydrogen gas volumetric fraction of 10% at normal pressure at 260° C. for 5 hours. After the completion of the reduction, the feeding was switched to the starting reaction material to carry out the reaction.

Example 16

The preparation of the Cu-based catalyst H'6 was as follows:

(1') The preparation of the catalyst precursor F'6 was carried out in the following steps:

(1'-1) 152 g of copper nitrate, 156 g nickel nitrate and 67 g of aluminum nitrate were dissolved in 1 L of deionized water to formulate a solution A'6. 33.6 g of potassium hydroxide was dissolved in 1 L of deionized water to formulate a solution B'6. 1 L of deionized water was added to a 5 L beaker, and warmed up and maintained at 80° C., and under a continuous stirring, to the beaker were added dropwisely the solutions A'6 and B'6, and the pH value was maintained at about 8.0. After the completion of the dropwise addition, the mixture was continuously stirred for 2 hours, then aged by standing for 2 hours, and filtered to produce a precipitate C'6.

(1-2) The precipitate C'6 was placed at 110° C. and dried for 24 hours, and then calcined at 400° C. for 5 hours. Then a graphite powder as lubricant was added in an amount of 3% by weight of the precipitate. The mixture was shaped by tabletting, and calcined at 400° C. for 5 hours to produce a cylindrical catalyst precursor D'6 having a diameter of 2.5-3.5 mm and a height of 2.5-3.5 mm.

(2) The preparation of the Cu-based catalyst H'6 was as follows:

(2-2-1) 0.77 g of acetoin was dissolved in 37.5 ml of methanol, and then 0.10 g of KOH was added to formulate a solution E'6. 10 g of the catalyst precursor D'6 (about 7.5 ml) was added to the solution E'6, and soaked under an ultrasonic condition for 5 hours;

(2-2-2) After the completion of the soaking in step (2-2-1), 70% by volume of the liquid in the solution E'5 was removed by evaporating at 70° C. to produce a catalyst precursor G'6.

(2-2-3) The catalyst precursor G'6 obtained in step (2-2-2) was loaded in a 20 ml stainless crystallization vessel. The crystallization vessel was kept under a self-generated pressure, and placed in an oven at 350° C. to let it stand for 24 hours;

(2-2-4) The catalyst precursor G'6 obtained after the treatment in step (2-2-3) was dried at 110° C. for 24 hours and calcined at 400° C. for 10 hours to produce a final catalyst H'6.

By elemental analysis, the catalyst H'6 had the CuO content by weight of 49.1%, the NiO content by weight of 39.7%, the K2O content by weight of 1.1%, the Al2O3 content by weight of 10.1%.

The catalyst H'6 was subjected to the following pre-treatment before it was used in the dehydrogenation reaction of dihydric alcohol to prepare the hydroxyketone: the catalyst was reduced with a mixed gas of nitrogen and hydrogen having a hydrogen gas volumetric fraction of 10% at normal pressure at 260° C. for 8 hours. After the completion of the reduction, the feeding was switched to the starting reaction material to carry out the reaction.

Examples 17-21

The pre-treated catalysts H'5 and H'6 obtained in Examples 15 and 16 were used as catalyst to investigate the effect of the reaction conditions on the reaction performance for the production of acetoin by the dehydrogenation of 2,3-butanediol under a critical hydrogen condition in a fixed bed reactor having an inner diameter of 10 mm. The experiment results were listed in Table 3.

TABLE 3

| Example | Catalyst | Reaction temperature (° C.) | Reaction pressure (MPa) | LHSV ($h^{-1}$) | Hydrogen to alcohol molar ratio | 2,3-butanediol conversion (%) | Acetoin selectivity (%) | Acetoin yield (%) |
|---|---|---|---|---|---|---|---|---|
| 17 | H'5 | 210 | 0.1 | 7.5 | 1 | 36.7 | 98.1 | 36.0 |
| 18 | H'5 | 230 | 0.1 | 10 | 1 | 47.9 | 97.7 | 46.8 |
| 19 | H'6 | 250 | 0.2 | 8.5 | 1 | 63.2 | 97.4 | 61.6 |
| 20 | H'6 | 270 | 0.1 | 6.5 | 1 | 66.1 | 96.3 | 63.7 |
| 21 | H'5 | 290 | 0.05 | 5 | 1 | 69.8 | 94.2 | 65.8 |

Example 22

The preparation of the Cu-based catalyst H'7 was as follows:

(1') The preparation of the catalyst precursor F'7 was carried out in the following steps:

(1'-1) 152 g of copper nitrate, 147 g of zinc nitrate and 60 g of aluminum nitrate were dissolved in 1 L of deionized water to formulate a solution A'7. 50 g of sodium carbonate was dissolved in 1 L of deionized water to formulate a solution B'7. 1 L of deionized water was added to a 5 L beaker, and warmed up and maintained at 95° C., and under a continuous stirring, to the beaker were added dropwisely the solutions A'7 and B'7, and the pH value was maintained at about 9.0. After the completion of the dropwise addition, the mixture was continuously stirred for 2 hours, then aged by standing for 2 hours, and filtered to produce a precipitate C'7.

(1'-2) The precipitate C'7 was placed at 110° C. and dried for 24 hours, and then calcined at 400° C. for 5 hours. Then a graphite powder as lubricant was added in an amount of 3% by weight of the precipitate. The mixture was shaped by tabletting, and calcined at 400° C. for 5 hours to produce a cylindrical catalyst precursor F'7 having a diameter of 3.5-4.5 mm and a height of 3.5-4.5 mm.

(2) The preparation of the Cu-based catalyst H'7 was as follows:

(2-2-1) 0.38 g of acetoin and 0.25 g of KOH were dissolved in 37.5 ml of methanol to formulate a solution G'7. 10 g of the catalyst precursor F'7 was added to the solution G'7, and soaked for 10 hours by stirring under an ultrasonic condition at room temperature (20-30° C.);

(2-2-2) After the completion of the soaking in step (2-2-1), 99% by volume of the liquid in the solution E'7 was removed by evaporating at 65° C. to produce a final Cu-based catalyst H'7. By elemental analysis, the catalyst H'7 had the CuO content by weight of 46.7%, the ZnO content by weight of 38.6%, the K2O content by weight of 1.7%, the Al2O3 content by weight of 9.4%, the acetoin content by weight of 1.7%, the methanol content by weight of 1.9%.

The catalyst H'7 was subjected to the following pre-treatment before it was used in the dehydrogenation reaction of dihydric alcohol to prepare the hydroxyketone:

(3-1) 10 g of the catalyst H'7 was loaded in a 20 ml stainless crystallization vessel, and nitrogen was introduced until the pressure reached 0.2 MPa. The crystallization vessel was placed in an oven at 325° C., and the treatment was carried out for 24 hours;

(3-2) The catalyst H'7 obtained after the treatment in step (3-1) was reduced with a mixed gas of nitrogen and hydrogen having a hydrogen gas volumetric fraction of 10% at normal pressure at 200° C. for 10 hours. After the completion of the reduction, the feeding was switched to the starting reaction material to carry out the reaction.

Example 23

Figure 2:
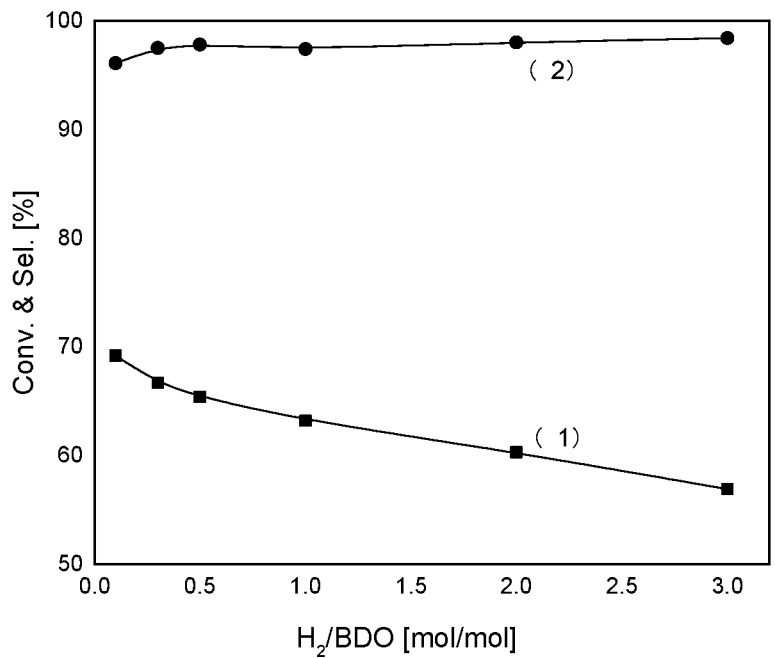
FIG. 2 shows the effect of the hydrogen to alcohol molar ratio (H2/BDO) on the 2,3-butanediol conversion (1) and the acetoin selectivity (2) as evaluated in Example 20.

The catalyst H'7 prepared in Example 22 was used as catalyst to investigate the effect of the hydrogen to alcohol molar ratio on the reaction performance for the production of acetoin by the dehydrogenation of 2,3-butanediol in a fixed bed reactor having an inner diameter of 10 mm. The reaction temperature was 270° C., and the reaction pressure was 0.1 MPa. The experiment results were listed in FIG. 2.

Example 24

Using acetoin as the starting material, the catalyst H1 prepared in Example 1 and the catalyst H'4 prepared in Example 10 were compared for the catalytic performance. The evaluation test was carried out in a micro-reactor having a volume of 1.67 ml, and the temperature of the reaction vessel was controlled by a fluidized bed sand bath furnace. The catalysts were pre-treated according to the pre-reduction and treatment procedures described in Example 1 and Example 10 respectively, prior to each catalyst evaluation. The specific catalyst evaluation process was as follows: 25 mg of acetoin, 25 mg of t-butanol and 5 mg of the catalyst were added to the reaction vessel, and sealed. The reaction vessel was placed in a fluidized bed sand bath furnace, which had been previously heated to the desired reaction temperature, to carry out the reaction. After reacting for 2 hours, the reaction vessel was taken out immediately and placed in cold water to cool the reaction vessel down. After the cooling was completed, the reaction vessel was opened. The substance in the reaction vessel was washed with acetone, and transferred to a 10 ml volumetric flask with a pipette to the marked volume. The mixture was filtered, and the resulting product was subjected to a quantitative analysis using GC-FID and a qualitative analysis using GC-MS. The reaction results were shown in Table 4.

TABLE 4

| Catalyst | Reaction temperature (° C.) | Acetoin conversion (%) |
|---|---|---|
| H'4 | 250 | 1.1 |
| H1 | 250 | 18.3 |

For the catalyst H1 prepared by the process of Example 1, the reaction product was analyzed by GC-MS, and a relatively large amount of the deep acetoin conversion products such as 2,3-butanedione (yield 10.3%) and methylpentanedione (yield 6.2%) were present in the product. However, the further conversion of acetoin could be greatly inhibited by using the catalyst preparation process disclosed in Example 10 of the present invention.

Example 24

The 2,3-butanediol dehydrogenation product obtained from Example 19 was separated by a vacuum distillation process well known to those skilled in the art to produce an acetoin product. The quality of the acetoin product was tested with the analytic method described in QB/T 4234-2011 "3-hydroxy-2-butanone (acetoin)", and the result was shown in Table 5.

TABLE 5

| Technical indexes | QB/T 4234-2011 Technical requirement | Acetoin product of Examples Measured value | Commercial available acetoin additive Measured value |
|---|---|---|---|
| Color and state | Colorless or pale-yellow liquid | pale-yellow liquid | pale-yellow liquid |
| Flavor | buttery flavor | buttery flavor | buttery flavor |
| Relative density (25° C./25° C.) | 0.994-1.019 | 1.012 | 1.010 |
| Refractive index (20° C.) | 1.4120-1.4200 | 1.4199 | 1.4195 |
| Content (GC) | ≥96.0% | 99.7% | 98.1 |
| Sulfur content (mg/L) | — | 0 | 0.4 |
| Nitrogen content (mg/L) | — | 0 | 1.0 |

As shown in Table 5, the acetoin product produced by the present invention conformed to the technical indexes of QB/T 4234-2011 "3-hydroxy-2-butanone (acetoin)", and the purity of acetoin was as high as 99.7%. Further, the acetoin product produced by the present invention contained no sulfur and nitrogen impurities as compared with the commercially available acetoin additive produced by the acetaldehyde condensation method, and was more suitable as food additive.

The invention claimed is:

1. A Cu-containing catalyst, the Cu-containing catalyst being obtained by contacting a catalyst precursor with acetoin and optionally a solvent prior to being reduced, wherein, based on a total weight of said catalyst precursor, said catalyst precursor comprises:
   30-60% of CuO,
   10-45% of $Yb_2O_3$,
   1-10% of an alkali metal (as oxide),
   0-30% of a binder (on a dry basis and as oxide),
   wherein, relative to 100 parts by weight of said catalyst precursor, said Cu-containing catalyst precursor contacting with 0.1-20 parts by weight of acetoin and less than 30 parts by weight of said solvent, and wherein contacting said catalyst precursor with acetoin is performed by
   i. contacting the catalyst precursor with a gaseous stream containing 1-10 vol % of acetoin at a temperature of 100-200° C. under a pressure of 0.1-5 MPa for 2-60 hours; or
   ii. impregnating the catalyst precursor with 1-5 vol % acetoin in methanol under ultrasonic mixing at 20-30° C. for 5-10 hrs.

2. The Cu-containing catalyst of claim 1, wherein said catalyst precursor comprises:
   40-50% of CuO,
   35-45% of $Yb_2O_3$,
   1-5% of said alkali metal (as oxide),
   5-15% of said binder (on a dry basis and as oxide), and relative to 100 parts by weight of said catalyst precursor, 0.1-5 parts by weight of acetoin and 3 parts by weight or less of said solvent contacting with the catalyst precursor.

3. The Cu-containing catalyst of claim 1, wherein the binder is at least one inorganic binder selected from alumina, bauxite, pseudo-boehmite, silica, silica-alumina, boehmite, attapulgite, bentonite, kaolin, diatomite, and montmorillonite.

4. A process for preparing the Cu-containing catalyst of claim 1, comprising:
(1) producing said catalyst precursor by subjecting a mixture containing a Cu precursor, $Yb_2O_3$ or a precursor thereof, an alkali metal precursor, and optionally a binder precursor to co-precipitation, and
(2-1) contacting acetoin with said catalyst precursor to produce said Cu-containing catalyst.

5. The preparation process of claim 4, wherein in said step (2-1), relative to 100 parts by weight of said catalyst precursor, acetoin is 0.1-20 parts by weight.

6. A process for preparing the Cu-containing catalyst of claim 1, comprising:
(1) an aqueous solution A' containing Cu, Al and ytterbium (Yb) is formulated, an aqueous solution B' containing a precipitant is formulated, the solution A' and the solution B' are added simultaneously under the continuous stirring condition, the precipitation temperature is controlled to 70-95° C., and the pH value is controlled to 8-9, after the completion of the dropwise addition, the resulting mixture is aged and filtered to produce a precipitate C';
(2) the precipitate C' obtained in step (1) is dried, shaped and calcined to produce a catalyst precursor D';
(3) a methanol solution containing acetoin is formulated, a predetermined amount of a hydroxide containing an alkali metal was added to formulate into a solution E', a predetermined amount of the catalyst precursor D' obtained in step (2) is added and soaked under an ultrasonic condition for 5-10 hours, after the completion of soaking, methanol in the solution E' is evaporated at 65-70° C. to dryness to produce a catalyst precursor F';
(4) the catalyst precursor F' obtained in step (3) is disposed in a closed vessel, and let it stand at a temperature of 300-350° C. for 24-48 hours to produce a catalyst precursor G';
(5) the catalyst precursor G' obtained in step (4) is dried to produce said Cu-containing catalyst.

7. The preparation process of claim 4, wherein the binder is at least one inorganic binder selected from alumina, bauxite, pseudo-boehmite, silica, silica-alumina, boehmite, attapulgite, bentonite, kaolin, diatomite, and montmorillonite.

8. The preparation process of claim 4, wherein said catalyst precursor comprises:
40-50% of CuO,
35-45% of $Yb_2O_3$,
1-5% of said alkali metal (as oxide), and
5-15% of said binder (on a dry basis and as oxide).

9. The preparation process of claim 5, wherein in said step (2-1), relative to 100 parts by weight of said catalyst precursor, acetoin is 0.1-5 parts by weight.

10. The preparation process of claim 4, wherein said acetoin is in a gaseous state or in form of a gas mixture.

11. A process for preparing a hydroxyketone compound, comprising a step of converting a dihydric alcohol represented by formula (I) to a hydroxyketone compound represented by formula (II) in presence of the Cu-containing catalyst of claim 1,

$R_1$-CH(OH)—CH(OH)—$R_2$ (I),

$R_1$-C(=O)—CH(OH)—$R_2$ (II), wherein the groups $R_1$ and $R_2$ are identical to or different from each other and each independently represents $C_{1-6}$ linear or branched alkyl,
wherein the converting step is carried out without a diluent at a temperature of 250-270° C. under a pressure of 0.01-0.2 MPa at a liquid hourly space velocity of 1.5-5 $h^{-1}$; or, the converting step is carried out in presence of a diluent at a temperature of 270-300° C. under a pressure of 0.01-0.2 MPa at a liquid hourly space velocity of 5-10 $h^{-1}$, and the molar ratio of said diluent to said dihydric alcohol represented by formula (I) of 0.1-3.

12. The preparation process according to claim 11, comprising a step of aging said Cu-containing catalyst for 2-60 hours at a temperature of 150-350° C. and under a pressure of 0.1-5 MPa prior to said conversion step.

13. The preparation process according to claim 11, comprising a step of reducing said Cu-containing catalyst in presence of hydrogen at a temperature of 200-400° C. and under a pressure of 0.1-10 MPa prior to said conversion step.

* * * * *